United States Patent
Lindgren et al.

(10) Patent No.: US 9,101,304 B2
(45) Date of Patent: Aug. 11, 2015

(54) ON-LINE MEASURING SYSTEM OF BODY SUBSTANCES

(75) Inventors: Stefan Lindgren, Vallentuna (SE); Anders Carlsson, Uppsala (SE); Anton Karlsson, Enskede (SE); Henrik Falkén, Lidingö (SE); Gerhard Jobst, Eichstetten (DE)

(73) Assignee: Maquet Critical Care AB, Solna (SE)

( * ) Notice: Subject to any disclaimer, the term of this patent is extended or adjusted under 35 U.S.C. 154(b) by 1226 days.

(21) Appl. No.: 13/000,708

(22) PCT Filed: Jul. 2, 2009

(86) PCT No.: PCT/SE2009/050863
§ 371 (c)(1),
(2), (4) Date: Feb. 25, 2011

(87) PCT Pub. No.: WO2010/002350
PCT Pub. Date: Jan. 7, 2010

(65) Prior Publication Data
US 2011/0213230 A1  Sep. 1, 2011

Related U.S. Application Data

(60) Provisional application No. 61/077,614, filed on Jul. 2, 2008, provisional application No. 61/077,617, filed on Jul. 2, 2008.

(30) Foreign Application Priority Data

Jul. 2, 2008  (SE) ........................................ 0801569
Jul. 2, 2008  (SE) ........................................ 0801571

(51) Int. Cl.
*A61B 5/00*  (2006.01)
*A61B 5/145*  (2006.01)
(Continued)

(52) U.S. Cl.
CPC ......... *A61B 5/14532* (2013.01); *A61B 5/14525* (2013.01); *A61B 5/14528* (2013.01); *A61B 5/14546* (2013.01); *A61B 5/14865* (2013.01); *A61B 5/412* (2013.01); *A61B 5/1495* (2013.01)

(58) Field of Classification Search
CPC ........... A61B 5/14525; A61B 5/14528; A61B 5/14532; A61B 5/14865
USPC ......................................................... 600/366
See application file for complete search history.

(56) References Cited

U.S. PATENT DOCUMENTS 5,957,839 A * 9/1999 Kruse et al. .................... 600/309
6,013,029 A * 1/2000 Korf et al. ...................... 600/363
(Continued)

FOREIGN PATENT DOCUMENTS

WO  2008-056363 A2  5/2008

OTHER PUBLICATIONS

Petrou et al, Biosensors and Bioelectronics, 17:859-865 (2002).
(Continued)

*Primary Examiner* — Michael D'Angelo
*Assistant Examiner* — Christian Jang
(74) *Attorney, Agent, or Firm* — Porter Wright Morris & Arthur LLP

(57) ABSTRACT

A measuring system (100) for continuously measuring body fluid constituents, said measuring system (100) comprising a microdialysis catheter or probe (110) comprising a microdialysis membrane (116) to be placed in a blood stream or in tissue fluid. The measuring system further comprises a flow through sensor (200) for continuously measuring the concentration of substances present in the fluid that has passed the microdialysis membrane (116). The measuring system (100) further comprises a waste container (126).

57 Claims, 17 Drawing Sheets

(51) Int. Cl.
*A61B 5/1486* (2006.01)
*A61B 5/1495* (2006.01)

(56) References Cited

U.S. PATENT DOCUMENTS

| | | |
|---|---|---|
| 2002/0082490 A1 | 6/2002 | Roeper et al. |
| 2003/0032874 A1* | 2/2003 | Rhodes et al. ............... 600/347 |
| 2003/0088166 A1* | 5/2003 | Say et al. ..................... 600/345 |
| 2004/0168934 A1 | 9/2004 | Schaupp et al. |
| 2005/0205422 A1* | 9/2005 | Moser et al. ............ 204/403.06 |
| 2005/0209518 A1* | 9/2005 | Sage et al. .................... 600/366 |
| 2005/0215871 A1* | 9/2005 | Feldman et al. ............. 600/309 |
| 2006/0083710 A1 | 4/2006 | Joerger et al. |

OTHER PUBLICATIONS

Rhemrev-Boom et al, Analyst, 126:1073-1079 (2001).

Ao et al, Microdialysis sampling of cytokines, Methods 38 (2006), pp. 331-341.

Heinemann, Continuous Glucose Monitoring by Means of the Microdialysis Technique: Underlying Fundamental Aspects, Diabetes Technology & Therapeutics, vol. 5, No. 4, pp. 545-561, 2003.

Supplementary European Search Report and Opinion from corresponding EP 09773865, dated Sep. 13, 2013.

* cited by examiner

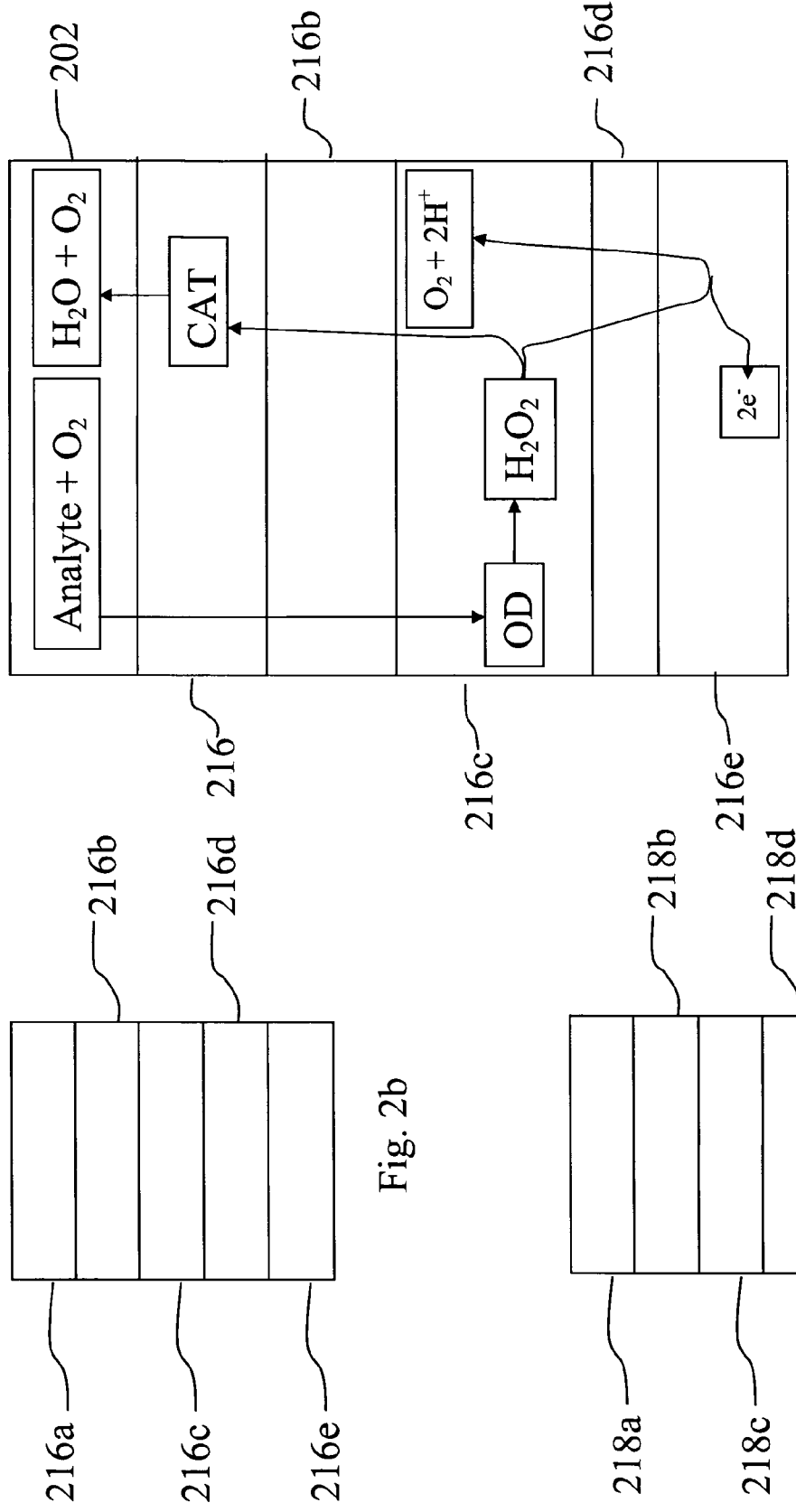

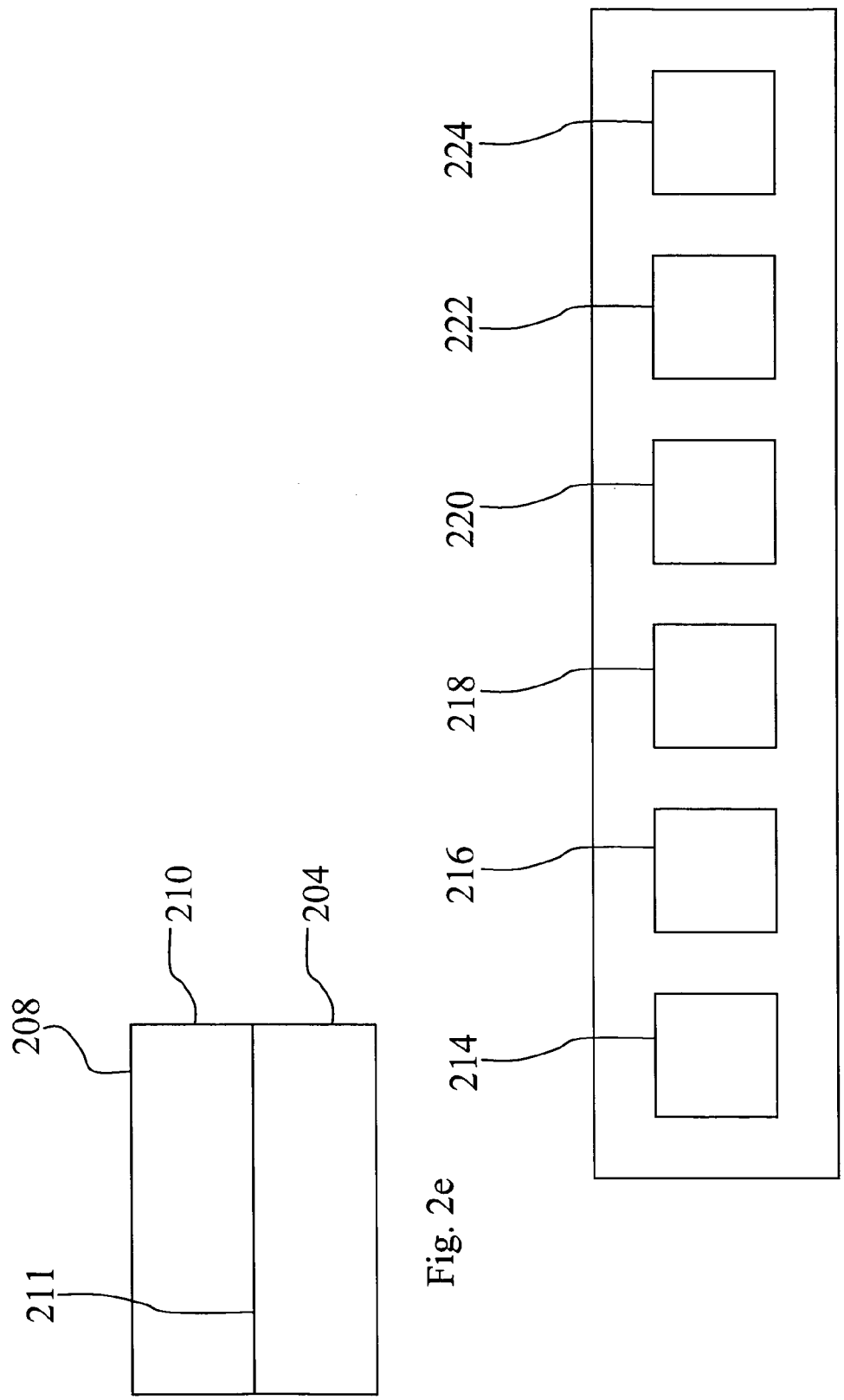

_US 9,101,304 B2_

ON-LINE MEASURING SYSTEM OF BODY SUBSTANCES

RELATED APPLICATIONS

The present application is a 371 of PCT/SE2009/050863 filed Jul. 2, 2009 and claims priority under 35 U.S.C. 119 of U.S. Applications Nos. 61/077,614 and 61/077,617, both of which were filed Jul. 2, 2008.

TECHNICAL FIELD

The present invention relates to a system for continuously measuring substances present in the body. More specifically, the system is suitable for measuring substances that are indicators of pathological conditions and the sampling probe of the system may be placed in the blood stream or in the tissue of an organ. The present invention also relates to a method of presenting measured values.

BACKGROUND

Since recently it is known that certain substances that may be present in the body can function as indicators for various pathological conditions in the body. Such substances are hereafter called indicator substances. Examples of indicator substances are glucose, lactate, pyruvate, glycerol, glutamate, and glutamine and heart specific enzymes. Pathological conditions that may be indicated or detected, or as well forecasted, include ischemia, hypoglycemia sepsis, cell membrane damage or lipolysis, vasospasms and metabolic disorders. By measuring indicator substances, pathological conditions may be detected before they lead to clinical signs. It may even be possible to detect processes or conditions that eventually may lead to a pathological condition. In many cases it would be advantageous to have the possibility to measure the concentration of indicator substances directly in a blood stream, or in tissue fluid. However, until now there have not existed any systems suitable for clinical use for measuring indicator substances. Systems known from the background art all have different drawbacks. Examples of common drawbacks in background art systems are that the measurement delay is extensive and that one has measured phenomena that are the result of a pathological condition, e.g. ischemia. This is clearly disadvantageous. With measurement delay is meant the time that passes from the moment that a sample is taken until the moment that a measurement value relating to this sample is obtained. In background art systems also measurement values can often only be obtained with relatively extended time periods, between each measurement value, e.g. if sample fluid is collected in micro vials. Faced with the aim or task to develop a reliable and accurate measuring system that can be used in monitoring the condition of a subject, e.g. a patient, in a critical condition or situation, the skilled person is faced with other problems and situations than those which previously have aroused.

From U.S. Pat. No. 5,078,135 there is known a measuring system where a drug is administrated to a rat and where a microdialysis probe is placed in the vein of the rat. Mass spectrometry is used to batchwise analyse the dialysate for obtaining pharmacokinetic data.

From US-A1-2004/0191848 there is known a system for measuring the concentration of glucose in tissue fluid. A microdialysis probe is used which is fed with a perfusate fluid already containing glucose. The concentration of glucose in the perfusate fluid is controlled using self-adaptive control.

It is an object to provide a measuring system that is improved with respect to the background art. A further object is to provide a system that is reliable and accurate to make the system suitable for clinical use with such suitable response times and the system is useful for on-line monitoring in critical care.

SUMMARY OF INVENTION

The above mentioned object and others may be obtained by providing a system measuring the concentration of substances or analytes in a body fluid or in a body tissue according to the independent claims attached below.

In general terms the system is provided with a microdialysis probe comprising a microdialysis membrane, both being adapted to be placed in blood or in tissue fluid. The probe is adapted to be invasively located in the body and to deliver perfusion fluid to and from the microdialysis membrane. The microdialysis probe of the system may be of the type disclosed in U.S. Pat. Nos. 6,264,627; 6,632,315; 6,346,090; 6,811,542; or in the Swedish patent application SE0602199-2. The probe dimensions may vary dependent on the selected clinical application and its location in the body. In a first embodiment, suitable for a cardiac catheter, the probe has a length of 55 cm and one inflow lumen and one outflow lumen where each lumen has an inner diameter of 0.15 mm. In another embodiment, suitable for a peripheral vein catheter, the probe has a length of about 10 cm and inner flow channels with diameter of about 0.15 mm. The system further includes a flow through sensor for analysing a fluid having passed said microdialysis probe and a pump for pumping the perfusion fluid to and through the microdialysis probe and to and through the sensor. A tubing connects the pump to the microdialysis probe and the microdialysis probe to the sensor. The pump generates a flow in the system with flow rate in the interval of 0.2-15 microliter per minute.

The tubing connecting the pump to the microdialysis probe has a length facilitating easy handling of the system. The inner diameter of the tubing is preferably adapted to the length so that the flow resistance or pressure drop of the tubing does not become too high. For the tubing connecting the pump to the microdialysis probe one suitable dimension is a length of about 1.5 m and an inner diameter of about 0.20 mm. This combination gives a flow resistance or pressure drop that is relatively low so that a relatively small motor can be used for the pump. This keeps power consumption low which is advantageous e.g. if the pump motor is battery powered.

For the tubing connecting the microdialysis probe to the sensor it is advantageous that the total volume of the bore of the tubing is small so that the time needed for a certain volume of dialysate to travel from the microdialysis probe to the sensor will be low, this makes the delay in the system low. But at the same time, flow resistance or pressure drop should be kept low enough. For this part of the tubing one suitable dimension is a length of about 10 cm and an inner diameter of about 0.15 mm. Since the tubing is short inner flow channel diameters of about 0.15 mm do not create any problems regarding flow resistance or pressure drop.

In an important general aspect of the invention, the flow through sensor comprises a flow channel with a flow resistance or pressure drop adapted to the characteristics of the microdialysis membrane so as to eliminate, or at least substantially reduce, ultra-filtering in the microdialysis membrane. Preferably, the cross-sectional area of the flow channel is adapted to one or more microdialysis membrane characteristics including the size or diameter of the pores in the microdialysis membrane, the membrane length and the liquid permeability of the membrane.

The system may comprise a waste container connected to the sensor. The tubing connecting the sensor to the waste container is suitably designed so as to have a flow resistance or pressure drop that is low enough considering the characteristics of the rest of the system, e.g. the characteristics of the microdialysis membrane. For this part of the tubing one suitable dimension is a length of about 1-2 cm and an inner diameter of about 0.15-0.20 mm. The dimensions for all parts of the tubing can of course be varied as suitable for the application at hand.

The sensor comprises a flow channel which has a flow resistance or pressure drop adapted to the characteristics of the microdialysis membrane so as to eliminate, or at least substantially reduce, ultra filtering in the microdialysis membrane.

According to one preferred embodiment, suitable for a peripheral vein catheter, the sensor flow channel has a flow resistance or pressure drop of less than about 100 Pa, suitably the flow rate in the system is about 0.5 microliters/minute and the microdialysis membrane has a liquid permeability, Lp, of about $2 \times 10^{-4}$ cm/bar×s, an active membrane length of about 30 mm and an outer diameter of about 0.59 mm. This results in the ultra filtering being less than 10 percent of the flow rate in the system, which is acceptable. If the flow rate would be higher than 0.5 microliters/minute the maximum allowable flow resistance or pressure drop, to reach the level of ultra filtering mentioned above, would be proportionally higher than 100 Pa assuming that the liquid permeability remains constant. If for example the flow rate would be about 1 microliters/minute, when the membrane has a liquid permeability of about $2 \times 10^{-4}$ cm/bar×s, and an active membrane length of about 30 mm, the maximum allowable flow resistance or pressure drop for the sensor flow channel would be about 200 Pa, to reach a level of ultra filtering that is lower than 10% of the flow rate.

According to another preferred embodiment, suitable for a central vein catheter, the sensor flow channel has a flow resistance or pressure drop less than about 1.6 kPa. Suitably, the flow rate in the system is about 10 microliters/minute and the microdialysis membrane has a liquid permeability, Lp, of about $2 \times 10^{-4}$ cm/bar$^x$s, and an active membrane length of about 40 mm. This results in the ultra filtering being less than 10 percent of the flow rate in the system, which is acceptable. If the flow rate would be higher than 10 micro liter/minute the maximum allowable flow resistance or pressure drop, to reach the level of ultra filtering mentioned above, would be proportionally higher than 1.6 kPa assuming that the liquid permeability remains constant. If for example the flow rate would be about 15 microliters/minute, when the membrane has a liquid permeability of about $2 \times 10^{-4}$ cm/bar$^x$s, and an active membrane length of about 40 mm, the maximum allowable flow resistance or pressure drop for the sensor flow channel would be about 2.4 kPa, to reach a level of ultra filtering that is lower than 10% of the flow rate.

According to another embodiment, the measuring system the microdialysis probe comprises a multilumen tube and a microdialysis membrane, wherein the tube exhibits at least two longitudinally arranged inner bores extending from a proximal end of the tube to the distal end of the tube. At least two channels are provided, one from each bore to the outside of the tube. The bores are blocked for passage of liquid distally of the respective channels. A tubular membrane is arranged circumferentially around the tube, so as to cover the at least two channels. The membrane is sealingly fastened to the tube so a space is formed between the tube and the membrane.

The flow channel is purposefully designed with respect to the desired flow rate and the microdialysis membrane. Suitably, in accordance with the present invention, the flow channel width is dimensioned in the interval of 250-1000 micrometer and with a flow channel height in the interval of 10 micrometer to 1 millimeter, advantageously in the interval of 25-100 micrometer. In accordance with a preferred embodiment, the dimension of the flow channel width is about 550 micrometer, and the dimension of the flow channel height is about 75 micrometer. On the other hand characteristics of the microdialysis membrane needs to be selected to fulfil requirements of the overall system performance. These characteristics comprise the size or diameter of the pores in the microdialysis membrane, the membrane length, the membrane outer diameter and the liquid (hydraulic) permeability of the membrane which is dependent on the number of membrane pores per unit membrane area (see N Lakshminarayanaiah in Biophysical Journal, 1967, Vol. 7, 1967, pages 511-526). Suitably, the membrane is made of a polyarlysulfonate, such as PAES (polyarylaethersulfonate) and it has a pore size adapted to the molecular size of the analyte, for example 10 nm for glucose/lactate. In an embodiment, especially suitable for analysis in whole blood, the membrane has its size exclusive layer located on the membrane outside, facing the body fluid. According to one embodiment, a suitable interval for the membrane outer diameter is about 0.2 mm to about 1.0 mm, even more suitable about 0.4 mm to about 0.8 mm. A suitable range for the liquid permeability of the membrane is about $1 \times 10^{-4}$ cm/bar×s to about $3 \times 10^{-4}$ cm/bar×s.

Since the membrane, and the microdialysis probe, has a relatively small outer diameter, around 0.59 mm in one embodiment, there is a substantial degree of flexibility regarding locating the microdialysis probe.

According to another embodiment, a suitable interval for the membrane outer diameter is 1-3 mm.

The sensor of the measuring system includes at least one measuring electrode with multiple membrane layers. The layers comprise an oxidase membrane layer with immobilized oxidase enzyme, such as glucose and/or lactate oxidase, capable of reacting the analyte with oxygen in a hydrogen peroxide generating reaction; and a diffusion limiting membrane adapted to provide a higher diffusion resistance for the analyte than for oxygen and provide lower flow of analyte to the oxidase membrane layer than the conversion rate of the oxidase enzyme. In a preferred embodiment the diffusion limiting membrane has a thickness of about 10 micrometer. Preferably, the diffusion limiting membrane is made from a hydrogel, preferably the hydrogel is poly-HEMA. The oxidase membrane layer has an area adapted so that the output signal of said measuring electrode is sufficiently high relative a potential noise level or noise signal for the lowest analyte concentration in the linear measurement range of the measuring electrode. Preferably, the oxidase membrane layer has an essentially circular area with a diameter from about 250-1000 micrometer, most preferably the area is about 450 micrometer. The sensor further preferably comprises a catalase membrane with a sufficient extension and catalase activity to substantially decompose all the hydrogen peroxide reaching the membrane. Preferably, the catalase membrane has a thickness in the interval of 5 to 10 micrometer.

In one aspect of the invention, the measuring system according to any claims comprises several consecutively arranged measuring electrodes and is dimensioned according to what has previously been outlined. For example two glucose electrodes and two lactate electrodes may be arranged together with a blank electrode (without any enzyme in the oxidase membrane) which is equally dimensioned according to the outlined requirements.

In another aspect of the invention the measuring system is provided with a waste container connected to an outflow end of the flow channel for collecting fluid flowing out from said flow channel. The waste container can comprise an absorbent which advantageously is anti bacterial. The waste container advantageously further comprises a pressure relief valve, advantageously impermeable to bacteria. The pressure relief valve may comprise a biocompatible polymeric material, preferably a polyethylene type material such as Tyvek™. Further, the waste container comprises means for connection to a receptacle for collecting fluid in said receptacle for further analysis of the fluid.

In a specially preferred embodiment the present invention is directed to a measuring system as outlined above that is essentially free from ultrafiltration when operated with a flow rate of about 0.5 microliter/min when continuously measuring and monitoring physiologically and clinically relevant levels of glucose and/or lactate with a sensor having a sensor flow resistance or pressure drop of less than about 100 Pa. According to this embodiment, the microdialysis membrane has an extension of about 30 mm active length and a liquid (hydraulic) permeability of about $2 \times 10^{-4}$ cm/bar×s; and the sensor flow channel has a flow channel with width of about 550 micrometer. Preferably, the flow channel length is about 7.5 mm.

In a another preferred embodiment the present invention is directed to a measuring system as outlined above that is essentially free from ultrafiltration when operated with a flow rate of about 10 microliter/min when continuously measuring and monitoring physiologically and clinically relevant levels of glucose and/or lactate with a sensor having sensor flow resistance less than 1.6 kPa. According to this embodiment, the microdialysis membrane has an extension of about 40 mm and a liquid (hydraulic) permeability of about $2 \times 10^{-4}$ cm/bar$^x$s; and the sensor flow channel has a flow channel with width of about 550 micrometer. Preferably, the flow channel length is about 7.5 mm.

Due to the design of the system, e.g. the chosen flow rate interval and that the characteristics of the different parts have been adapted to the flow rate interval and to each other, a system suitable for monitoring in critical or intensive care has been achieved. For example have the membrane area and the membrane liquid permeability been adapted to the flow rate interval and the sensor has been adapted to the rest of the system, e.g. the membrane characteristics.

One advantage of the present system is that the condition of an organ can be efficiently supervised or monitored when e.g. surgery is being, or has been, performed on the organ. It is interesting to monitor any organ but some examples are e.g. heart, liver and kidney. The system may also be used for central metabolic monitoring or peripheral arterial monitoring.

The significance of the different parts of the system and its sensor function is described in further detail in the following sections. Further possible features and benefits of the present invention will also be explained.

BRIEF DESCRIPTION OF THE DRAWINGS

The invention will now be described by way of non limiting exemplary embodiments and with reference to the accompanying drawings in which:

FIGS. 2b-2f are basic drawings showing different aspects of the sensor 200,

DETAILED DESCRIPTION OF THE INVENTION

Before the system described herein is described in detail, it is to be understood that this system is not limited to the particular component parts of the devices described or steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" also include plural referents unless the context clearly dictates otherwise. Thus, for example, reference to "an element" includes more than one such element, and the like.

Figure 1A:
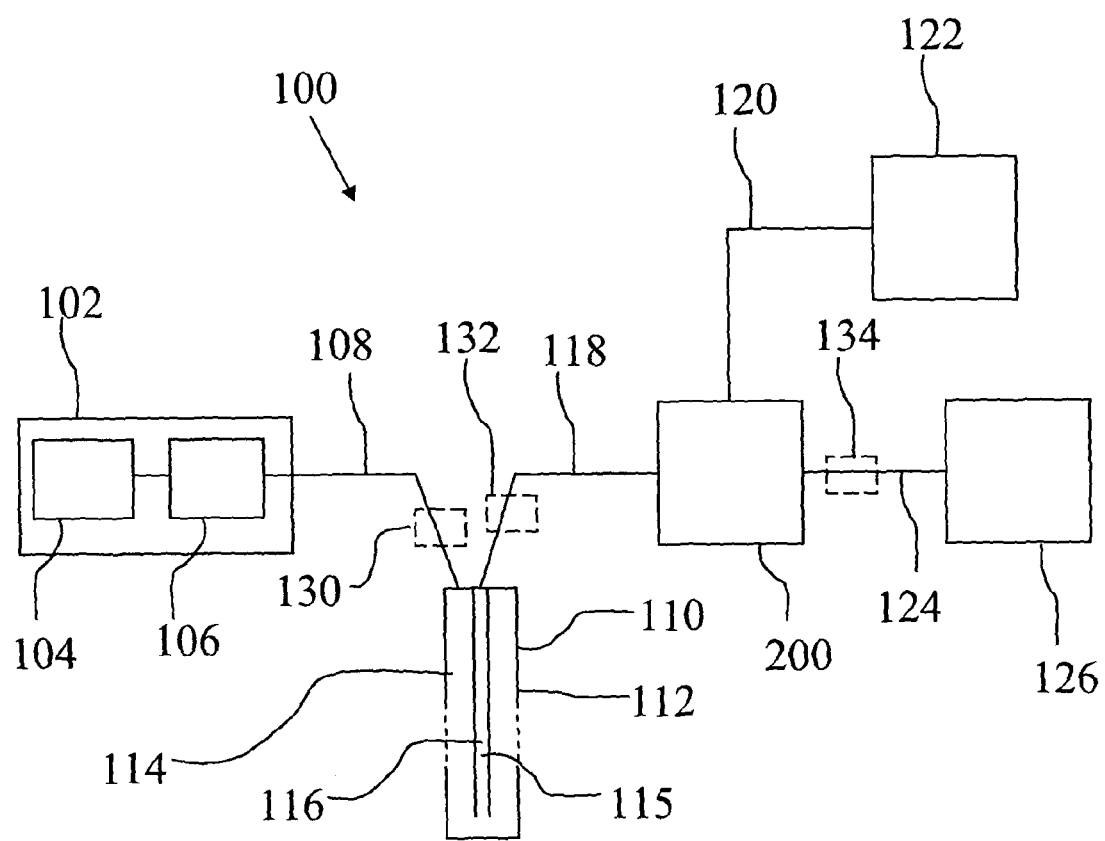
FIG. 1A is a drawing showing one embodiment of the system.

An embodiment of the measuring system 100 will now be described referring to FIG. 1A. The measuring system 100 is a push system, i.e. the fluid is pushed through the entire system 100 by the pump 106. This renders the system less complex than push-pull systems where the pushing action of one pump has to be coordinated with the pulling action of another pump. One feature in the measuring system 100 contributing to making it possible to realise the measuring system 100 as a push system is that the sensor 200 has a flow resistance or pressure drop that is adapted to the rest of the system, e.g. the microdialysis membrane 116. The microdialysis probe 110 of the system 100 may be adapted to be placed in a blood stream but may also be adapted to be placed in organ tissue. The system comprises a pump unit 102 including a perfusate reservoir 104 and a pump 106. Two suitable pumps are the CMA400 and CMA402 from the company CMA Microdialysis, Solna, Sweden. The pump unit 102 is connected to a microdialysis probe 110 via a piece of tubing 108. The pump 106 may as well in itself include the perfusate reservoir 104 which, as a suitable size, may accommodate a perfusate volume of about 5 ml.

It may be suitable to mount the perfusate reservoir 104 and the pump 106 substantially vertical, the part of the pump 106 that is connected to the tubing 108 being the lowest point. This is to allow air that may be present in the perfusate to escape upwards through the pump 106 and/or perfusate reservoir 104.

The microdialysis probe 110, which is shown in section, comprises a double bore tube 112 having an inner bore 115 and an outer bore 114 comprising a microdialysis membrane 116. The perfusate is supplied through the outer bore 114 and passes the microdialysis membrane 116 whereby microdialysis with the fluid surrounding the microdialysis membrane 116 takes place. After the microdialysis membrane 116 the perfusate is called dialysate. The dialysate 202 exits the microdialysis probe 110 through the inner bore 115. The dialysate 202 is conveyed to sensor 200 via a piece of tubing 118.

The sensor 200 is an electrochemical sensor of flow through type. A monitor or display 122 is connected to the sensor 200, via an electrical or optical cable 120 or via a wireless connection. The monitor or display 122 may comprise means for processing and displaying measurement values received from the sensor 200. The measurement values received from the sensor 200 may be displayed without processing but it may also be displayed e.g. mean values and derivatives of the measurement values. Different ways of displaying measurement values are however known to the person skilled in the art and need not to be further described here. To the sensor 200 there is also connected a waste container 126 for collecting the dialysate that has passed through the sensor 200. The dialysate 202 in the waste container can be used to perform measurements that was not performed by the sensor 200, e.g. to measure the concentration of substances that were not, or could not be, measured by the sensor 200. Examples of such substances are low molecular drugs and low molecular endogenous substances, e.g. amino acids, urea, creatinin. The waste container 126 suitably comprises a pressure release valve 126:2 which is placed in the opening 126:1 and is permeable to air but is a barrier to bacteria that may be present in the dialysate 202. It is also suitable that the waste container 126 comprises an absorbent 126:3 on the inside of the container, to absorb the dialysate that enters the waste container 126. Suitable the absorbent 126:3 is antibacterial, the absorbent may be placed on the inside of the upper and lower wall of the waste container 126 as shown at 126:3a and 126:3b. The pressure release valve 126:2 may comprise a piece of the material Tyvek covering the opening 126:1. If the dialysate 202 should be further analysed a microvial may be connected to the tubing 124 connected to the waste container 126 and protruding into the waste container. If the pressure release valve 126:2 comprises a piece of Tyvek, the Tyvek may be cut open and the microvial introduced into the waste container 126 through the created hole, and connected to the tubing 124.

The microdialysis membrane 116 may be of a type that is adapted to be placed in a blood stream. Alternatively, it is of a type that is adapted to be placed in organ tissue. In the background art, many membranes for microdialysis have shown a certain tendency to be clogged when placed in a blood stream. The inventors of the present system have therefore chosen a particular membrane for the case that the membrane should be placed in a blood stream, a membrane of the skin out type. Membranes for microdialysis have a selective layer that decides the size of molecules with capacity to pass the membrane wall. This selective layer traditionally is located on the inside of the membrane. However, this makes the membrane susceptible of being clogged when placed in a blood stream. In a membrane of the skin out type the selective layer is placed on the outside of the membrane which prevents the membrane from being clogged when placed in a blood stream. A suitable membrane 116 for the system 100 is a polyarylethersulfonate (PAES) membrane with a liquid permeability, Lp, of about $2 \times 10^{-4}$ cm/bar×s, available from Gambro, Lund, Sweden.

As an advantageous additional measure to prevent clogging of the microdialysis membrane 116, low molecular weight heparin (Lmwh heparin), e.g. dalteparin, may be added to the perfusate. If the microdialysis probe 110 is not placed in a blood stream but e.g. in the tissue of an organ, membranes of the non-skin out type may be used.

Figure 1B:
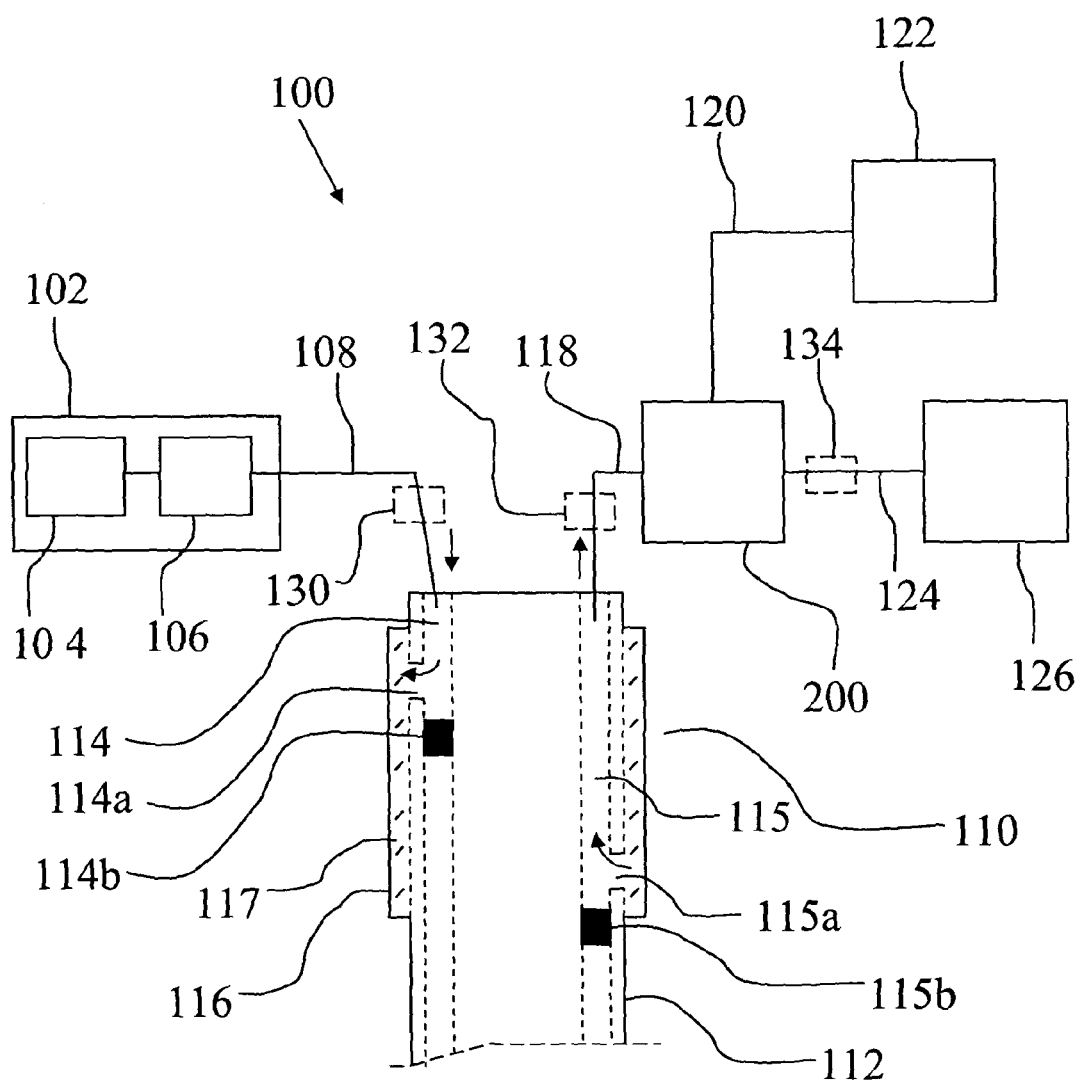
FIG. 1B is a drawing showing another embodiment of the system.

Another embodiment of the measuring system 100 will now be described referring to FIG. 1B. The measuring system 100 is a push system, i.e. the fluid is pushed through the entire system 100 by the pump 106. This renders the system less complex than push-pull systems where the pushing action of one pump has to be coordinated with the pulling action of another pump. One feature in the measuring system 100 contributing to making it possible to realise the measuring system 100 as a push system is that the sensor 200 has a flow resistance or pressure drop that is adapted to the rest of the system, e.g. the microdialysis membrane 116. The measuring probe 110 of the system 100 is advantageously adapted to be placed in a blood stream. To reach an organ, the microdialysis probe 110 often has to be relatively long, in many cases 50-90 centimeters. In the case of a microdialysis probe to be placed in the venous blood flow out of the heart, the probe is suitably 50-70 centimeters long. The system comprises a pump unit 102 including a perfusate reservoir 104 and a pump 106. The perfusate reservoir may be in the form of a syringe, one suitable syringe is the BD Plastipak 20 ml from the company BD, Franklin Lakes, N.J., United States. One suitable pump is the Fresenius Pilot C, from the company Fresenius Kabi AG, Bad Homburg, Germany. The pump unit 102 is connected to a microdialysis probe 110 via a piece of tubing 108. The pump 106 may as well in itself include the perfusate reservoir 104 which, as a suitable size, may accommodate a perfusate volume of about 20 ml.

It may be suitable to mount the perfusate reservoir 104 and the pump 106 substantially vertical, the part of the pump 106 that is connected to the tubing 108 being the lowest point. This is to allow air that may be present in the perfusate to escape upwards through the pump 106 and/or perfusate reservoir 104.

The microdialysis probe 110, which is shown in section, comprises a tube 112 having a first bore 114 and a second bore 115, the tube 112 comprising a microdialysis membrane 116. Between the outside of the tube 112 and the inside of the microdialysis membrane 116 there is a space 117. The perfusate is supplied through the first bore 114, exits the first bore 114 through a first channel 114a, enters the space 117 and passes the microdialysis membrane 116 whereby microdialysis with the fluid surrounding the microdialysis membrane 116 takes place. After the microdialysis membrane 116 the perfusate is called dialysate. The dialysate 202 exits the space 117 through a second channel 115b and exits the microdialysis probe 110 through the second bore 115. A blocking 114b in the first bore 114 directs the perfusate to enter the first channel 114a. A blocking 115b in the second bore 115 directs the dialysate 202 to exit the microdialysis probe 110 through the second bore 115. The dialysate 202 is conveyed to sensor 200 via a piece of tubing 118.

The sensor 200 is an electrochemical sensor of flow through type. A monitor or display 122 is connected to the sensor 200, via an electrical or optical cable 120 or via a wireless connection. The monitor or display 122 may comprise means for processing and displaying measurement values received from the sensor 200. The measurement values received from the sensor 200 may be displayed without processing but it may also be displayed e.g. mean values and derivatives of the measurement values. Different ways of displaying measurement values are however known to the person skilled in the art and need not to be further described here. To the sensor 200 there is also connected a waste container 126 for collecting the dialysate that has passed through the sensor 200. The dialysate 202 in the waste container can be used to perform measurements that was not performed by the sensor 200, e.g. to measure the concentration of substances that were not, or could not be, measured by the sensor 200. Examples of such substances are low molecular drugs and low molecular endogenous substances, e.g. amino acids, urea, creatinin. The waste container 126 suitably comprises a pressure release valve 126:2 which is placed in the opening 126:1 and is permeable to air but is a barrier to bacteria that may be present in the dialysate 202. It is also suitable that the waste container 126 comprises an absorbent 126:3 on the inside of the container, to absorb the dialysate that enters the waste container 126. Suitable the absorbent 126:3 is antibacterial, the absorbent may be placed on the inside of the upper and lower wall of the waste container 126 as shown at 126:3a and 126:3b. The pressure release valve 126:2 may comprise a piece of the material Tyvek covering the opening 126:1. If the dialysate 202 should be further analysed a microvial may be connected to the tubing 124 connected to the waste container 126 and protruding into the waste container. If the pressure release valve 126:2 comprises a piece of Tyvek, the Tyvek may be cut open and the microvial introduced into the waste container 126 and connected to the tubing 124.

The microdialysis membrane 116 is suitably adapted to be placed in a blood stream. In the background art, many membranes for microdialysis have shown a certain tendency to be clogged when placed in a blood stream. The inventors of the present system have therefore chosen a particular membrane for the case that the membrane should be placed in a blood stream, a membrane of the skin out type. Membranes for microdialysis have a selective layer that decides the size of molecules with capacity to pass the membrane wall. This selective layer traditionally is located on the inside of the membrane. However, this makes the membrane susceptible of being clogged when placed in a blood stream. In a membrane of the skin out type the selective layer is placed on the outside of the membrane which prevents the membrane from being clogged when placed in a blood stream. A suitable membrane 116 for the system 100 is a polyarylethersulfonate (PAES) membrane with a liquid permeability, Lp, in the range of about $1 \times 10^{-4}$ cm/bar$^x$s to about $3 \times 10^{-4}$ cm/bar$^x$s, available from Gambro, Lund, Sweden Membranes for microdialysis have a porous structure and the openings in the membrane are not well-defined channels but rather openings in the membrane that wary in size as one moves through the membrane. How large a molecule can be and still be able to pass through a membrane also depend on the shape of the molecule, and not only on the size. If a membrane has pores with a stated size of e.g. 10 nm that means that the size of the pores is around 10 nm. One suitable interval for the size of the pores is 5 to 50 nanometer (nm), even more suitable 10 to 30 nm. The lower limit is suitably around 10 nm so that bigger molecules like e.g. glucose still can pass the membrane. The upper limit is chosen so that the risk for ultra filtering is kept low. Ultra filtering is a situation where perfusate penetrates through the membrane and may occur when the pressure of the perfusate is too high in relation to the size of the pores in the membrane. The smaller the pores are, the higher the pressure of the perfusate can be without risking ultra filtering. One suitable size of the pores is around 10 nm when glucose is the analyte.

Figure 2A:
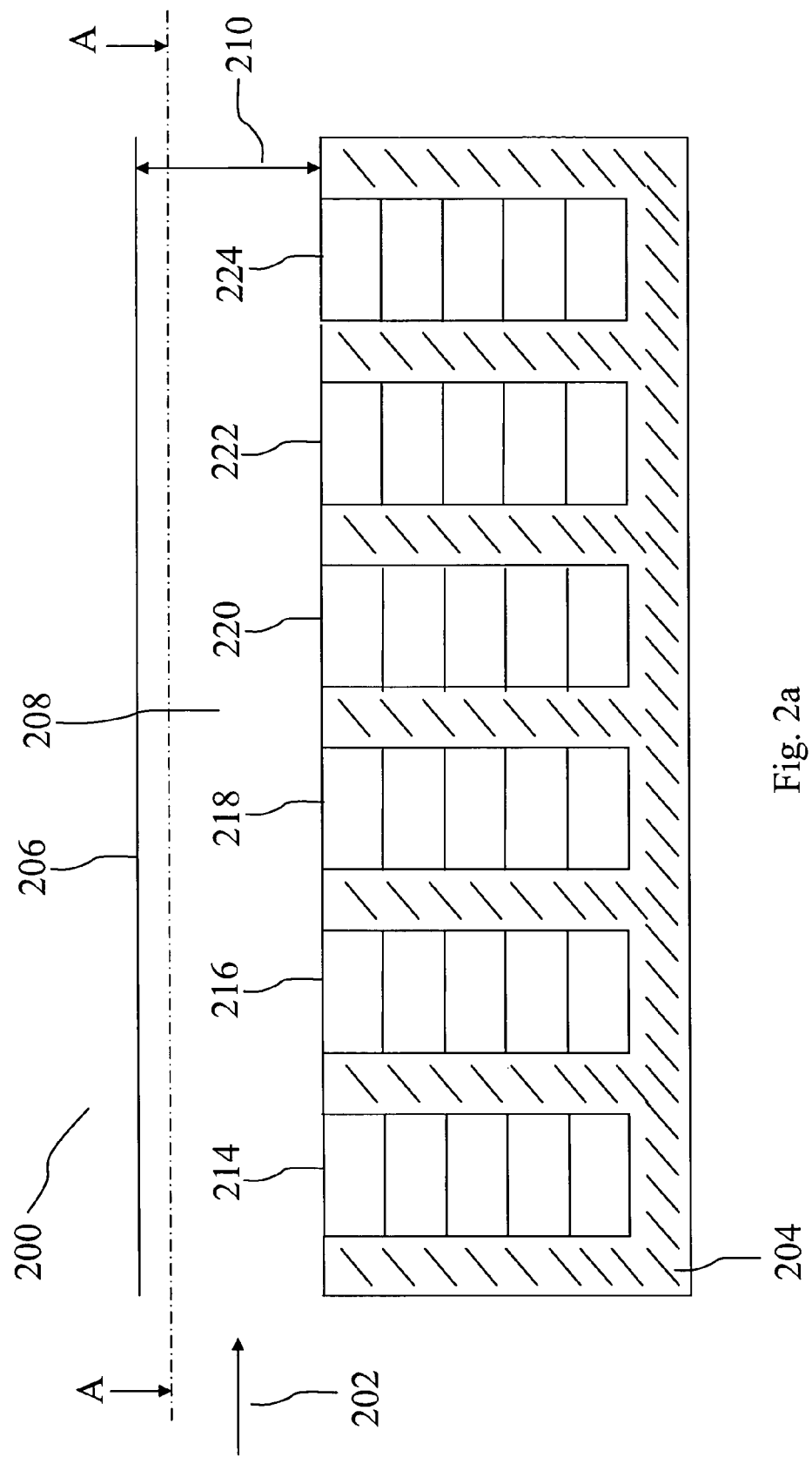
FIG. 2a is a basic drawing showing a section of a sensor 200.

With reference to FIGS. 2a-2f one first suitable embodiment of the sensor 200 will be described. FIG. 2a is a drawing schematically showing a section of the sensor 200. FIGS. 2b and 2c are drawings schematically showing detailed views of the sensor electrodes 216 and 218. FIG. 2d gives a schematic view of the main reaction and transport pathways of a measuring electrode in the sensor 200. FIG. 2e is a drawing schematically showing a front view of the sensor 200, indicating the flow channel height 210 and the flow channel width 211 of the flow channel 208. FIG. 2f is a drawing schematically showing the sensor 200 from above, according to cut or section A-A in FIG. 2a.

The sensor 200 comprises a carrier 204 and a cover 206. Reference sign 202 indicates the inflow of dialysate from the microdialysis probe 110. In the sensor 200 a flow channel 208 is defined, the height of the flow channel is indicated at 210. The flow channel also has a specified width which is indicated by 211 in FIG. 2e. In this first embodiment the sensor 200 comprises blank electrodes 214 and 220 and measuring electrodes 216, 218, 222 and 224. Namely a first blank electrode 214, a first lactate electrode 216, a first glucose electrode 218, a second blank electrode 220, a second lactate electrode 222 and a second glucose electrode 224. Measuring both glucose and lactate may be advantageous for detecting certain disadvantageous conditions in the body. The sensor 200 may also comprise measuring electrodes for only one indicator substance, or for more than two substances, depending on the application.

With reference to FIGS. 2b, 2c and 2d the design and function of the measuring electrodes will be described more in detail. Short description of the different membranes/layers in the measuring electrode 216:

216a: Catalase membrane
216b: Enzyme-free diffusion limiting membrane
216c: Oxidase membrane, here lactate oxidase membrane
216d: Selectively permeable membrane
216e: Platinum anode The dialysate 202 contains among other substances the analyte, e.g. glucose or lactate, and oxygen ($O_2$). In the oxidase membrane 216c a reduction/oxidation (redox) process takes place involving the analyte and the oxygen. In this redox process the analyte is oxidized and the oxygen is reduced. The products of this process are hydrogen peroxide and the oxidation product of the analyte. The oxidation product of the analyte diffuses out to the dialysate 202 and is washed away with the flow of the dialysate 202. A part of the hydrogen peroxide diffuses upwards in the measuring electrode 216 and another part diffuses towards the platinum anode 216e.

Oxidase Membrane 216c

The layer 216c is in this case a lactate oxidase membrane since the measuring electrode 216 is measuring lactate. This layer is a membrane in which the enzyme lactate oxidase is immobilized, preferably the membrane is a pHEMA-hydrogel membrane (pHEMA=Poly 2-Hydroxyethylmethacrylate). In the oxidase membrane 216c the immobilized enzyme lactate oxidase acts as a catalyst when the lactate that reaches the oxidase membrane 216c reacts with oxygen and hydrogen peroxide is produced. Some of the hydrogen peroxide that is produced diffuses upwards in the direction of the enzyme-free diffusion limiting membrane 216b and the catalase membrane 216a. When this hydrogen peroxide reaches the catalase membrane 216a it is decomposed by the catalase membrane 216a into oxygen and water. The two membranes diffusion limiting membrane 216b and catalase membrane 216a are described more in detail below.

Selective Membrane 216d

The layer 216d is a selective membrane that only, or at least substantially only, is permeable to hydrogen peroxide. Advantageously the layer 216d is an electropolymerized permselective membrane. The selective membrane 216d is advantageous since it suppresses electrochemical interference, otherwise there would be a risk that other substances than hydrogen peroxide could reach the platinum anode 216e and give rise to erroneous readings regarding the concentration of lactate in the dialysate 202. The hydrogen peroxide penetrates through the selective membrane 216d and is oxidised to oxygen at the platinum anode 216e. The oxidation of the hydrogen peroxide is achieved since the platinum anode 216e has a certain electrochemical catalytic activity. The products of the oxidation of one molecule of hydrogen peroxide ($H_2O_2$) are one molecule of oxygen, 2 electrons and 2 protons. This can be written as:

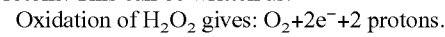
Oxidation of $H_2O_2$ gives: $O_2 + 2e^- + 2$ protons.

The electrons are the output of the sensor, the flow of electrons is measured and is used as the output signal of the sensor.

Hence, at the platinum anode 216e the hydrogen peroxide is detected and the amount of hydrogen peroxide detected is proportional to the amount of lactate present in the dialysate 202. Depending on the amount of hydrogen peroxide reaching the platinum anode 216e within a certain time period, different amounts of electrons per time period is produced, and hence gives different levels of the output signal.

Diffusion Limiting Membrane 216b

The layer 216b is an enzyme-free diffusion limiting membrane, advantageously a pHEMA-membrane, for controlling the diffusion of the analyte, e.g. lactate. The diffusion limiting membrane 216b controls how quickly the lactate, or how much lactate per time-period that, reaches the oxidase membrane 216c. In the dialysate 202 the concentration of oxygen is much lower than the concentration of the analyte. One common situation is to have a concentration of 5 to 10 mmol/l of the analyte, e.g. lactate, and a concentration of 0.2 millmoles of oxygen. If this difference in concentration would be present in the oxidase membrane 216c, there would not be enough oxygen present for the redox process in the oxidase membrane.

Therefore the diffusion limiting membrane 216b suitably reduces the diffusion speed or rate for oxygen to be 3 to 5 times lower than without the membrane 216b and suitably reduces the diffusion rate for the analyte, e.g. lactate or glucose, to be around 1000 times lower than without the membrane 216b. The reason why the diffusion limiting membrane 216b can hinder the diffusion of the analyte much stronger than the diffusion of the oxygen is that the oxygen molecules are much smaller than the molecules of the analyte. By choosing an appropriate material and thickness of the diffusion limiting membrane 216b, the above mentioned difference in limitation of diffusion rate can be achieved.

Because of this difference in reducing diffusion speed or rate the diffusion limiting membrane 216b brings the positive effect that the concentrations of oxygen and analyte is more in balance after the diffusion limiting membrane 216b, i.e. in the oxidase membrane 216c, which is desirable since it can be ensured that there is sufficient, or a surplus of, oxygen present for the redox process in the oxidase membrane 216c.

By controlling the diffusion rate of the analyte, here lactate, the amount of hydrogen peroxide that is produced in the oxidase membrane 216c can be controlled and be limited to a suitable level. The diffusion rate of the analyte is suitably controlled so that the oxygen present in the oxidase membrane 216c is not consumed too quickly and so that the immobilized enzyme is not saturated with analyte, e.g. lactate. At which diffusion rate of the analyte the immobilized enzyme gets saturated is indicated by the factor $K_m$, the higher the value of $K_m$, the more analyte per time period the immobilized enzyme can process or transform. Hence, $K_m$ is a characteristic of the immobilized enzyme.

The inventors unexpectedly concluded that increasing the diffusion resistance of the enzyme-free diffusion limiting membrane 216b increased the useful life of the immobilized enzyme in the oxidase membrane 216c. One reason for this is that the immobilized enzyme is sensitive to hydrogen peroxide, the immobilized enzyme is degenerated by the produced hydrogen peroxide. This is especially the case for the immobilized lactate enzyme. By increasing the diffusion resistance of the diffusion limiting membrane 216b the amount of lactate that reaches the oxidase membrane 216c per time unit is reduced and hence the production per time unit of hydrogen peroxide is limited and the degeneration of the immobilized lactate enzyme is limited. The amount of hydrogen peroxide that is produced is suitably limited so that the immobilized enzyme is not degenerated too fast, which may become a drawback depending on with which application the sensor is used.

The enzyme-free diffusion limiting membrane 216b also increases the diffusion resistance for hydrogen peroxide that moves towards the catalase membrane 216a. That reduces the load on the catalase membrane 216a caused by the hydrogen peroxide that reaches the catalase membrane 216a.

By adjusting the diffusion resistance, e.g. by adjusting the thickness and/or the size of the channels, of the enzyme-free diffusion limiting membrane 216b the measurement interval for which the measuring electrode is linear can be adjusted. By increasing the diffusion resistance, the maximum limit in analyte concentration, in the dialysate 202, for which the measuring electrode responds linearly is increased. However, if the diffusion resistance is increased too much, the accuracy and sensitivity for low concentrations of the analyte decreases.

Figure 4:
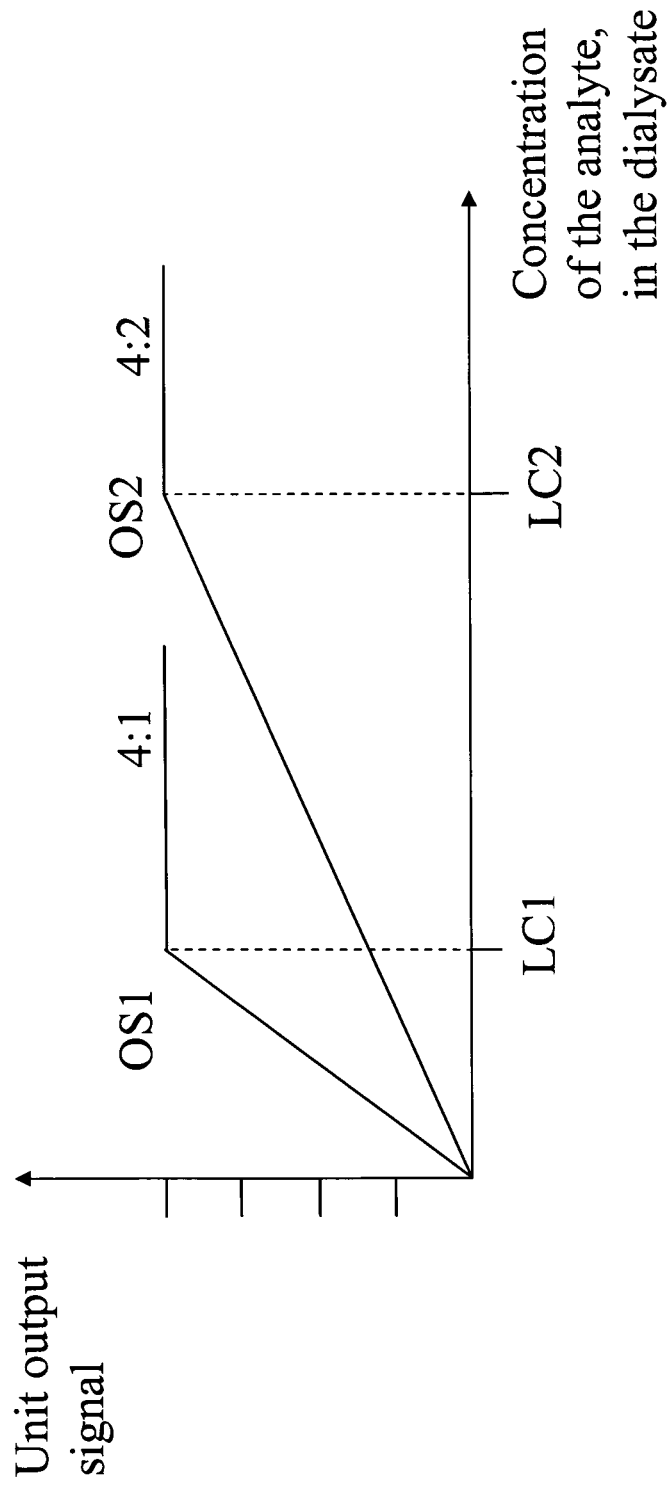
FIG. 4 is a drawing schematically showing output signals for different thicknesses of the diffusion limiting membrane 216b, FIGS. 5a and 5b schematically show one embodiment of the waste container 126.
Figure 5B:
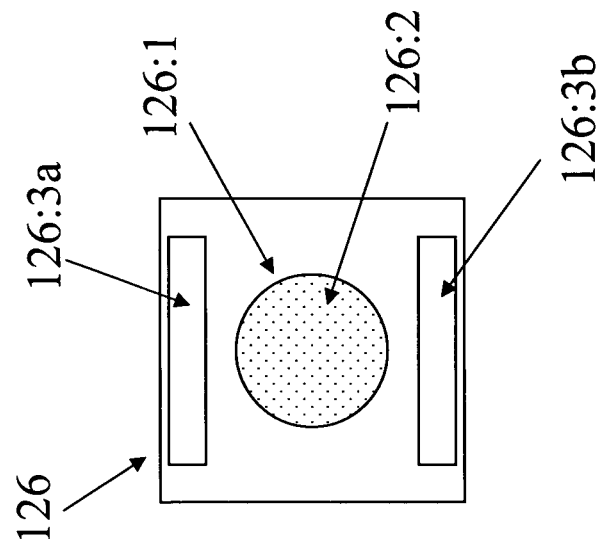
FIG. 5a shows the waste container 126 in section from above and FIG. 5b shows the waste container from behind, FIGS. 6a-6f demonstrates results with a system according to the invention from venous blood of a test animal.
Figure 5A:
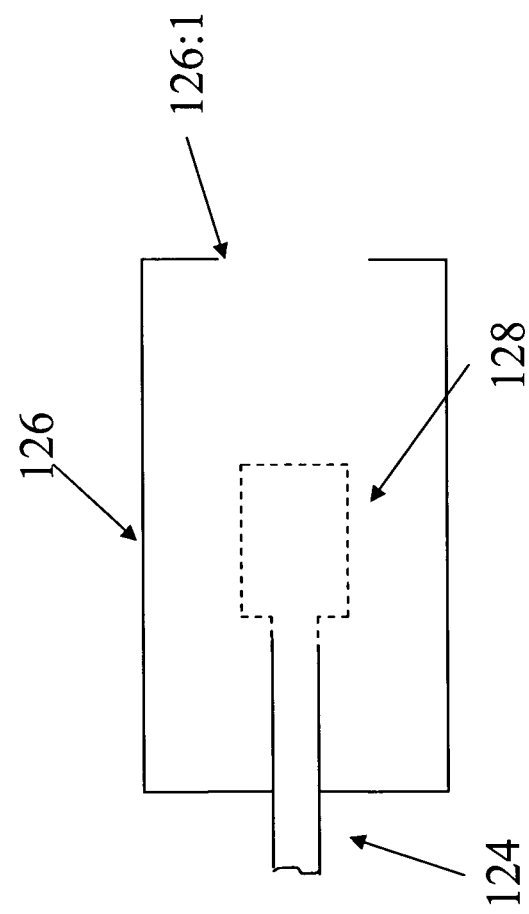

FIG. 4 schematically shows output signals for different thicknesses of the diffusion limiting membrane 216b and where OS1 means output signal 1, OS2 means output signal 2, LC1 means limit concentration 1, LC2 means limit concentration 2. Curve 4:1 represents an output signal obtained with a diffusion limiting membrane 216b that has a smaller thickness as compared to the diffusion limiting membrane used when obtaining curve 4:2. The curves 4:1 and 4:2 are only schematically drawn and illustrate that different thicknesses of the diffusion limiting membrane 216b give different linearity intervals and different inclinations of the curves. For curve 4:1 the linearity interval is from approximately zero concentration up to point LC1, For curve 4:2 the linearity interval is from approximately zero concentration up to point LC2. In reality the transition from the linear part of the curves to the horizontal part, after LC1 respectively LC2, may be a bit curved. The horizontal part of the curves represent the situation that the immobilized enzyme is saturated with analyte.

Also, the response time for the measuring electrode increases if the diffusion resistance increases since total processing time in the measuring electrode will be longer.

Sensor Layout

One possibility is also to have a sensor with several measuring electrodes for each measured substance, e.g. 2 or 3 measuring electrodes for lactate. In this way each measuring electrode can be optimized for a certain interval of the concentration of the analyte (e.g. glucose, lactate, pyruvate, glycerol, glutamate or glutamine) in the dialysate. A higher thickness of the enzyme-free diffusion limiting membrane 216b makes it possible to measure higher concentrations of a substance or analyte present in the dialysate but to measure low concentrations of a substance, the thickness of the enzyme-free diffusion limiting membrane 216b must not be too high so that the measuring electrode has the sensitivity necessary to obtain reliable measurements also for low concentrations of a substance present in the dialysate.

Catalase Membrane

The catalase membrane 216a prevents hydrogen peroxide diffusing upwards from the oxidase membrane 216c from reaching the dialysate 202 and in this way prevents cross-talk between the different measuring electrodes. Hydrogen peroxide that reaches the catalase membrane 216a from the oxidase membrane 216c is decomposed within the catalase membrane 216a. The catalase membrane 216a also brings an extremely low flow rate dependency because hydrogen peroxide that otherwise would accumulate within the dialysate 202 is decomposed in the catalase membrane 216a. The very low flow rate dependency is advantageous in achieving a high accuracy. If hydrogen peroxide would accumulate within the dialysate 202, this would lead to an increase in the sensor signal measured at the platinum anode 216e. This is a problem in measuring electrodes having no catalase membrane 216a covering the oxidase membrane 216c. The flow rate dependency in those measuring electrodes makes it difficult to obtain a measuring electrode with high accuracy. If there would be no catalase membrane 216a hydrogen peroxide would accumulate in the dialysate 202 above the measuring electrode 216 and would, at least partially, diffuse down through the measuring electrode 216 and increase the sensor signal. How much of the hydrogen peroxide accumulated in the dialysate 202 that would diffuse down through the measuring electrode 216 would be dependent on the flow rate of the dialysate 202. Hence, the output signal of the measuring electrode would be dependent on the flow rate of the dialysate 202.

The first glucose electrode 218, the second lactate electrode 222 and the second glucose electrode 224 function in a similar way or according to the same principles as the first lactate electrode 216.

Since the sensor 200 has a very low flow rate dependency the flow rate in the system can be allowed to vary to a certain extent. This is advantageous since the pump 106 do not have to deliver a very exact flow rate. This makes the pump less complex, which is advantageous in view of reliability, and less costly.

The characteristics of the sensor 200 need to be adapted to the characteristics of the microdialysis membrane 116. One aspect is that the flow resistance or pressure drop of the sensor 200 can not be too high. If the flow resistance or pressure drop of the sensor 200 would be too high, the pressure in the system would be too high and the perfusate flowing passed, or through the bore of, the microdialysis membrane 116 could be pressed or pushed through the microdialysis membrane 116. This is called ultra filtration. This would be disadvantageous since the measuring function of the system 100 would be hampered or negatively affected. Or the system 100 could even be completely non-functional. Another disadvantageous aspect is that it is not acceptable that the subject of the measurement, e.g. a patient in an ICU, is injected with the perfusate. From the view of safety for the subject, the perfusate should not enter the subject, even if perfusates are non-hazardous.

To ensure that the flow resistance or pressure drop in the sensor 200 is low enough, the cross sectional area of the flow channel 208 must be sufficiently large. However, a certain flow resistance or pressure drop in the sensor 200 is acceptable or even suitable, e.g. since a certain pressure will be built up so air bubbles that may form in the dialysate 202 will be dissolved quicker than if there would be no pressure in the dialysate 202. Air bubbles may form in the dialysate 202 when the fluid is warmed up. A certain pressure in the dialysate 202 will facilitate that the deformation will take place in a shorter time period and the air bubble will be resolved quicker.

If the height of the flow channel is low, there is a high possibility that an air bubble will be deformed, since there is little space available for the air bubble, and for a shallower flow channel a higher force is exerted on an air bubble. In that way the air bubble becomes destabilized and dissolves. If an air bubble would be present on the surface of a measuring electrode it would reduce the diffusion of the analyte down through the measuring electrode and result in a erroneous reading.

However, if an air bubble would be so large that it covers the whole, or substantially the whole, area of a measuring electrode the value recorded by the measuring electrode would drop rapidly, possibly to approximately zero depending on how long the air bubble would stay on the surface of the electrode, such a reading can be identified as erroneous and be discarded.

One advantageous measure for the flow channel 208 is a flow channel height 210 of approximately 75 micrometer and a flow channel width 211 of approximately 450 micrometer. A suitable interval for the flow channel width 211 is 250 to 1000 micro meters. A flow channel width 211 of 250 micrometer is a suitable lower limit since that width still renders the area of the oxidase membrane 216c sufficiently large. With a smaller flow channel width 211 than 250 micrometer problems may be encountered with a too low signal level from the sensor because resulting from a small production of hydrogen peroxide in the oxidase membrane 216c due to a too small area of the oxidase membrane 216c. This depends on the lowest analyte concentration that the measuring electrode should be able to detect with sufficient accuracy. The oxidase membrane 216c may have a circular or essentially circular shape, as seen in the direction of the arrows at "A" in FIG. 2a. In this case a suitable interval for the dimensions of the oxidase membrane is a diameter of 250-1000 micrometer, suitably 250-700 micrometer, most preferably about 450 micrometer. A flow channel width of 1000 micrometer is a suitable upper limit to limit the internal volume in the system to advantageously limit the delay in the system.

A suitable interval for the flow channel height 210 is 10 micrometer to 1 millimeter, ever more suitable is 25 to 100 micrometer, The measures flow channel height 210 of approximately 75 micrometer and a flow channel width 211 of approximately 450 micrometer, render the flow channel 208 a flow resistance or pressure drop of less than about 100 Pa, which is the maximum flow resistance or pressure drop suitable for a skin out microdialysis membrane 116 with an Lp coefficient of 2 when operated with a flow rate of about 0.5 microliter/minute and having an active membrane length of about 30 mm, to reach a level of ultra filtration that is not too high, suitably lower than 10% of the flow rate.

It is suitable that the cover 206 of the flow channel 208 comprises a relatively rigid material, so that the flow resistance or pressure drop do not vary, at least not substantially. Having a stable flow resistance or pressure drop of the flow channel 208 makes the system 100 more reliable since that eliminates or reduces the risk for a pressure build up under the microdialysis membrane 116 due to an increase in flow resistance or pressure drop. As explained previously, a pressure build up under the microdialysis membrane 116 is disadvantageous since that may cause ultra filtering, if the pressure reaches too high levels.

The length of the sensor 200 is governed by the space required for the different measuring electrodes.

There is a risk that air bubbles could be formed in the dialysate flow, as also mentioned previously. As previously discussed air bubbles can be counteracted by selecting appropriate flow channel dimensions, but can further be counteracted by selecting a hydrophilic channel material. In terms of delay in the system 100 it is preferred that the internal volume of the flow channel 208 is low and represent a low internal volume. A suitable flow channel height for these purposes in the present system is about 75 micrometer. Also the relatively high flow rate is an advantage regarding air bubbles since the relatively high flow rate helps to wash away the air bubbles. The relatively high flow rate may also be suitable in applications where the tubing and/or microdialysis probe is relatively long, so as to transport the fluid through the system in an appropriate way and avoiding air to hinder the fluid flow.

There are also other aspects influencing the design of the sensor 200. A measuring electrode needs to have a certain minimum area because the oxidase membrane (e.g. the oxidase membrane 216c) needs to have a certain minimum area so that the production of hydrogen peroxide will be high enough and thereby give a signal level from the measuring electrode that is high enough. If the signal level from the sensor becomes too low problems with noise levels present in the electronics connected to the sensor may arise, in the sense that the noise level could be too high in relation to the signal level from the sensor. The platinum anode 216e also gives rise to a certain noise level. One reason is that the platinum anode has a certain capacitance. Since the platinum anode 216e has some capacitance it is suitable that the electronics connected to the platinum anode has a constant voltage, or a voltage that varies as little as possible. The fact that the oxidase membrane needs to have a certain minimum area leads to that the flow channel 208 needs to have a certain minimum width for the measuring electrode to have reasonable dimensions, a reasonable relationship between length and width. Since it is suitable that the flow channel 208 has small dimensions, but it is suitable that the oxidase membrane has a fairly big area, a compromise has to be done so that the area of the oxidase membrane will be high enough, and the flow channel 208 small enough. Suitably the platinum anode 216e has the same area as the oxidase membrane 216c.

The blank electrodes 214 and 220 have a design similar to the measuring electrodes but is free from enzyme in layers 214c, 220c. In these layers there is only the membrane material, e.g. a hydrogel membrane, present wherein the immobilized enzymes are kept in the measuring electrodes. One reason for providing the first blank electrode 214 is to detect any hydrogen peroxide, or other electroactive substances, e.g. ascorbic acid or paracetamol, present in the dialysate 202 already before the dialysate 202 arrives to the measuring electrodes, in order to establish a reference level for the signals obtained from the measuring electrodes. If the output signal from the first blank electrode 214 would be very high that may be a sign of a error in the system and the output signals from the measuring electrodes obtained at that point of time can be discarded, if appropriate.

By providing two electrodes each for lactate and glucose redundancy is achieved and the reliability and accuracy of the system 100 is improved since if a fault arises in one measuring electrode, the other can still be used. It is more unlikely that two measuring electrodes should be erroneous than that an error occurs in one measuring electrode. By comparing the readings or sensor signals from two measuring electrodes measuring the same substance it can be determined if the measuring electrodes function correctly, or if one of them gives an erroneous reading. The possibility to detect such erroneous readings increases the accuracy of the system 100 since the probability to have access to a sensor signal from a properly functioning measuring electrode is increased.

One reason for providing the second blank electrode 220 is to detect any potential cross talk between the measuring electrodes. That is, e.g. to detect potential hydrogen peroxide present in the dialysate in the flow channel 208. If for example the catalase membrane of one of the first measuring electrodes would not function properly hydrogen peroxide from that measuring electrode could enter into the flow channel 208. Such a situation can be detected by comparing the signals from the first blank electrode 214 and the second blank electrode 220.

The first glucose electrode 218 has a design similar to the first lactate electrode 216. The second lactate electrode 222 has in one embodiment the same design as the first lactate electrode 216 and the second glucose electrode 224 has in one embodiment the same design as the first glucose electrode 218. But other designs are of course also possible, e.g. several measuring electrodes for the same analyte but having different linear ranges.

The diffusion rate in a measuring electrode is temperature dependent. The higher the temperature in the measuring electrode is, the higher the diffusion rate will be. This means that also the output signal from a measuring electrode is temperature dependent, the higher the diffusion rate is, the higher the output signal will be for a given concentration of the analyte in the dialysate. It is therefore advantageous to determine the temperature of the measuring electrode to enable a correction of the output signal with respect to the determined temperature. A temperature sensor, not shown, may be placed on the carrier 204 to determine the temperature. It can be assumed that the measured temperature is valid for all measuring electrodes in the sensor. This approximation often gives an accuracy that is high enough. It may be suitable to calibrate the sensor 200/measuring electrodes as close to the normal operating temperature as possible, e.g. at 35 degrees Celsius, to obtain a calibration that is as accurate as possible. An accurate calibration makes it possible to accurately adjust the output signal with respect to the effect of the temperature of the measuring electrode.

Figure 3:
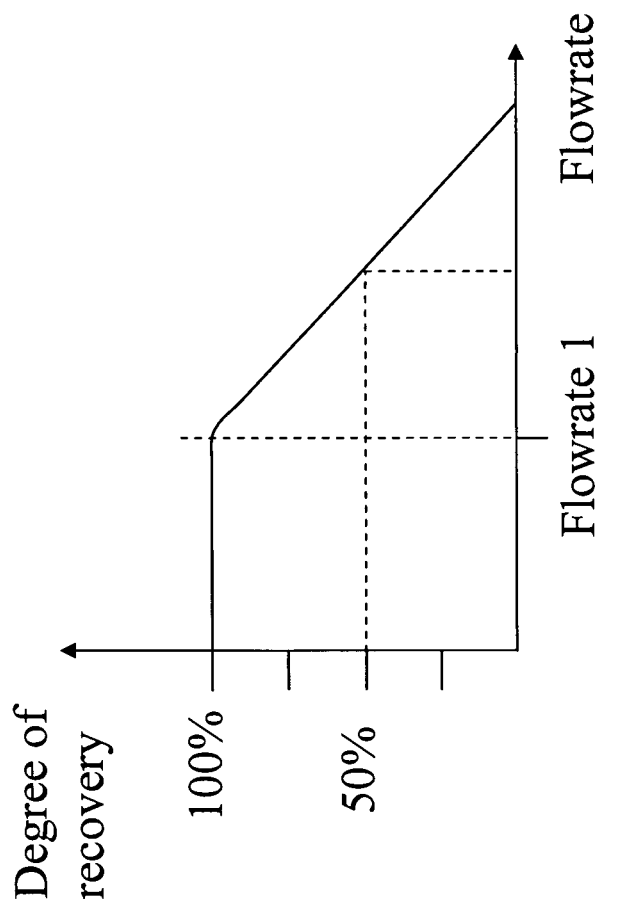
FIG. 3 is a basic drawing showing the relationship between flow rate and degree of recovery for a microdialysis membrane.

FIG. 3 is a basic drawing schematically showing the relation between flow rate and recovery degree in, or relating to, a microdialysis membrane. As seen in the Figure, for lower flow rates and up to a certain maximum flow rate, flow rate 1, 100% recovery degree is achieved. A recovery degree of 100% means that there is an equilibrium between the concentration of a certain substance in the fluid outside of the microdialysis membrane and the concentration of this certain substance in the fluid on the inside of the microdialysis membrane. In the present system 100 the flow rate has been chosen to be lower than the value flow rate 1. A flow rate in the interval of about 0.2-2.0 microliters per minute has been found to be suitable, more suitable 0.3-1.5 microliters per minute and even more suitable 0.5-1.0 microliters per minute. One suitable flow rate that has been used is about 1.0 microliter per minute. Another flow rate in the interval of about 5-15 microliters per minute has also been found to be suitable, more suitable 8-12 microliters per minute and even more suitable 9-11 microliters per minute. One suitable flow rate that has been used is about 10 microliter per minute. One advantage of this choice of flow rate is that a low delay is achieved, which often is an advantage in intensive or critical care applications. With a flow rate of about 10 microliter per minute a delay of approximately 2 minutes was achieved when the length of tubing 118 between the microdialysis probe 110 and the sensor 200 was 25 cm. A low delay is advantageous to achieve an early detection of a potentially pathological or dangerous condition in an organ of a subject. These choices of flow rate has a number of advantages. Firstly the flow rate may vary without resulting in a variation in recovery. As said previously, this enables the use of a pump with a less complex construction. That the flow rate may vary is also facilitated by the fact that the sensor 200 has a very low flow rate dependency, as mentioned previously.

With a flow rate value below flow rate 1, accuracy is improved as compared to a situation where the flow rate is higher than flow rate 1, since it is always assured that the recovery is 100%. In a system where the flow rate is higher than flow rate 1 the flow rate has to be controlled to be within narrow limits so that the concentration in the fluid surrounding the microdialysis membrane can be calculated using the specific degree of recovery, e.g. maybe 50%, corresponding to the flow rate value prevailing in the system. The control of the flow rate is however of course not perfect and a slight variation in flow rate can not be excluded. Hence, a certain inaccuracy is introduced.

In a measuring electrode 216, 218, 222, 224, the immobilized enzyme in the oxidase membrane, e.g. the oxidase membrane 216c, often functions best in an environment with a pH around 7. This is e.g. the case for the enzymes lactate and glucose oxidase. But when the hydrogen peroxide ($H_2O_2$) in a measuring electrode enter the selective membrane, e.g. selective membrane 216d, protons are formed. When not counteracted, protons would change the pH to be unfavourable for the immobilized enzyme in the oxidase membrane. However, since the flow rate is low and 100% recovery degree is achieved in the present system 100, buffering substances from the fluid, e.g. blood, surrounding the microdialysis membrane 116, can fully enter the perfusate. Sufficient buffering substances, e.g. bicarbonate, will then be present in the dialysate flow 202 in the flow channel 208 to neutralise protons, thereby avoiding acidification resulting in poor functionality of the immobilized enzyme. In systems where insufficient buffering substances enter through the microdialysis membrane, buffering substances have to be added to the dialysate after the microdialysis probe. This is a potential drawback since it makes the system more complex and potentially less reliable.

As described above, the design of the sensor 200 been carried out in order to create a well functioning system 100 where the design of the sensor 200 has been adapted to the other parts and aspects of the measuring system 100, e.g. the microdialysis membrane 116 and the suitably flow rate of 0.2-15 microliters/min. One advantage with the measuring system 100 is that measurement values or sensor signals can be obtained very often, several times each second if desired. This is advantageous in assessing the condition in a critically ill subject, for example a person being monitored or treated in an ICU, where a change of condition needs urgent detection and therapy. Further the inventive measuring system admits a very low measurement delay, meaning the time period from the moment at which a certain volume of perfusate/dialysate passes the microdialysis membrane 116, until the moment the concentration of a certain substance in this volume of dialysate can be detected by monitoring the sensor signal from a measuring electrode. This measurement delay can be approximately 3 minutes. Depending on the design of the system, e.g. the flow rate, the length of the tubing, the volume of perfusate/dialysate in the system, this measurement delay can be changed to be shorter or longer, depending to the requirements.

Figure 6A:
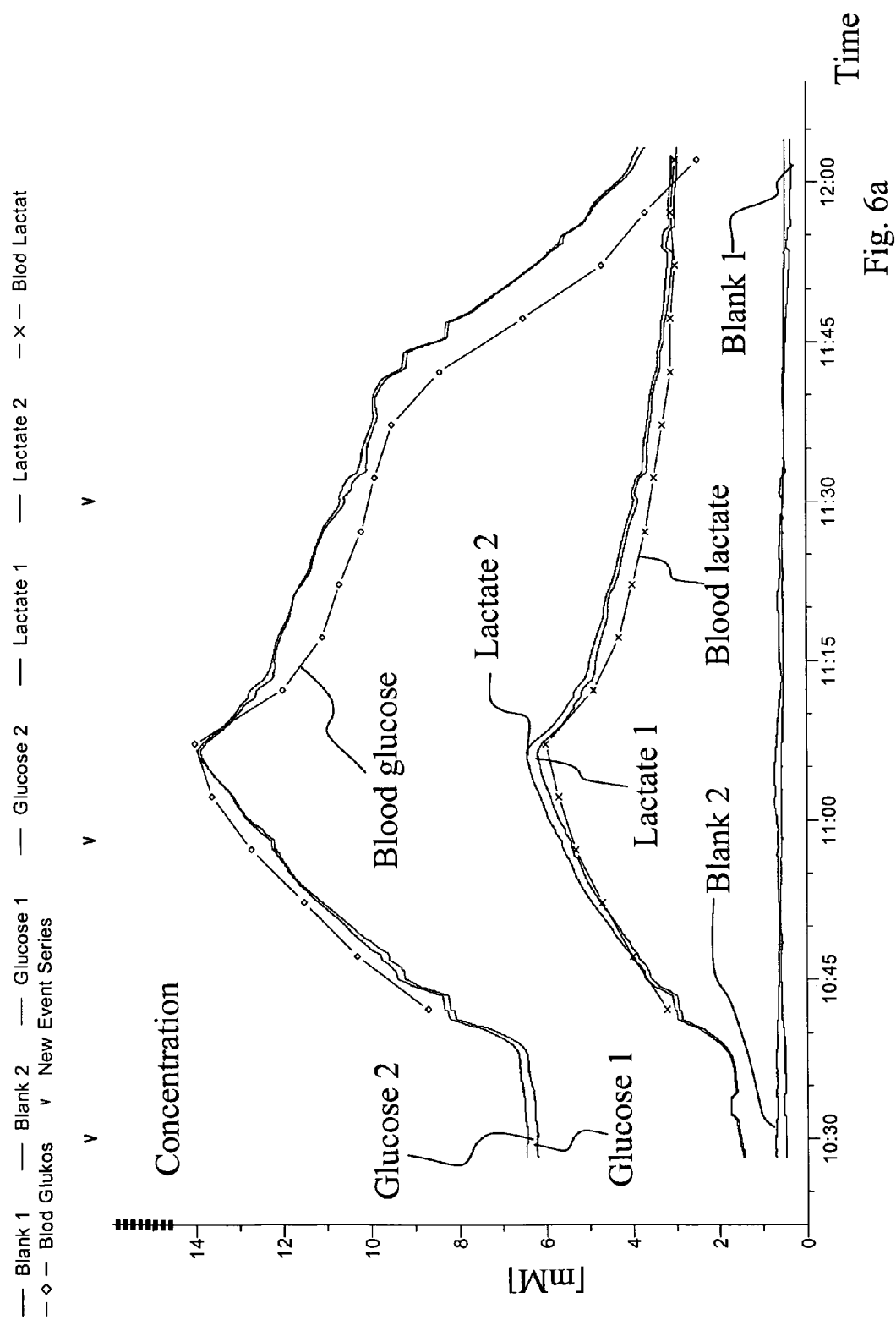
Figure 6B:
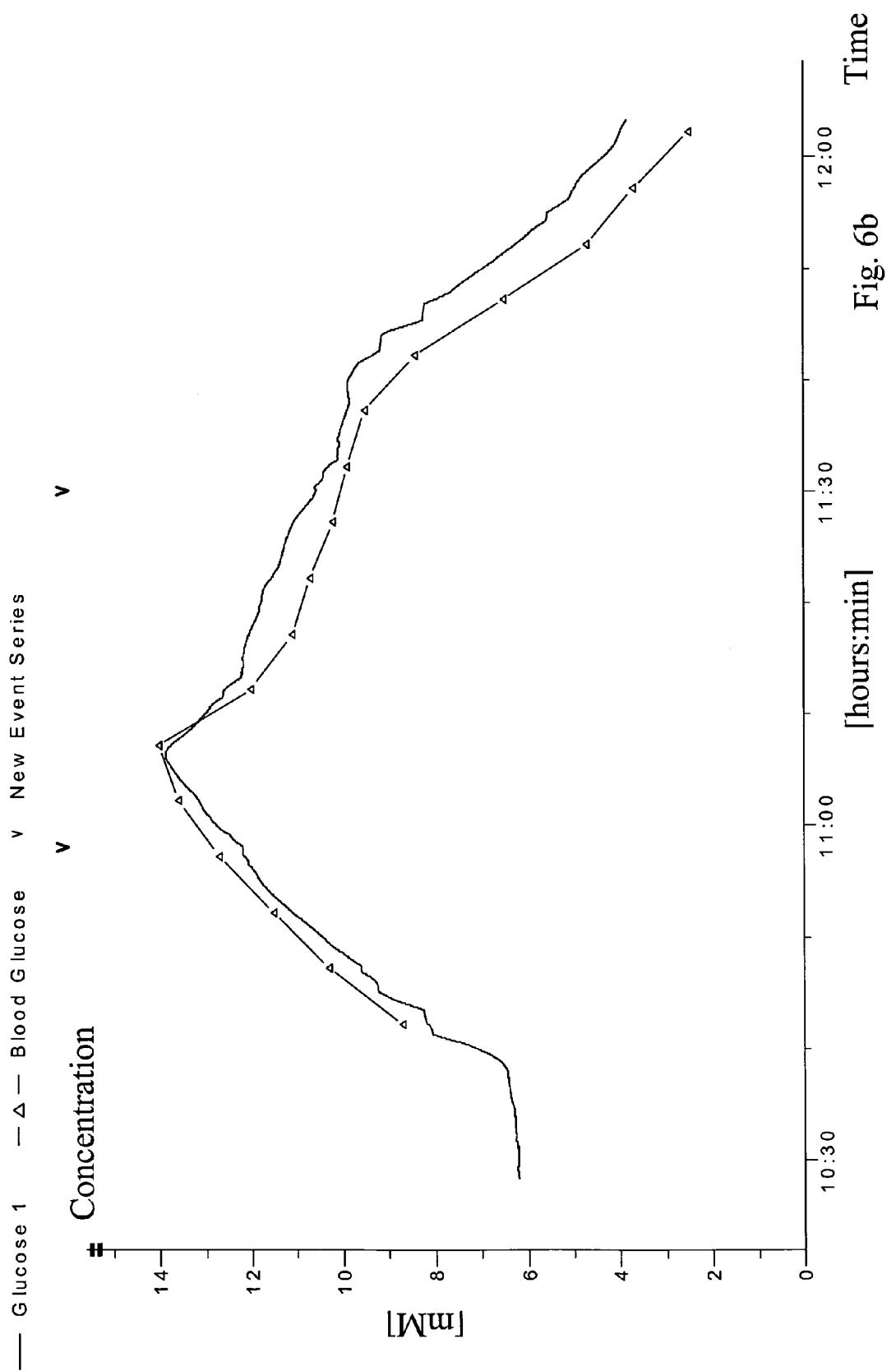
Figure 6C:
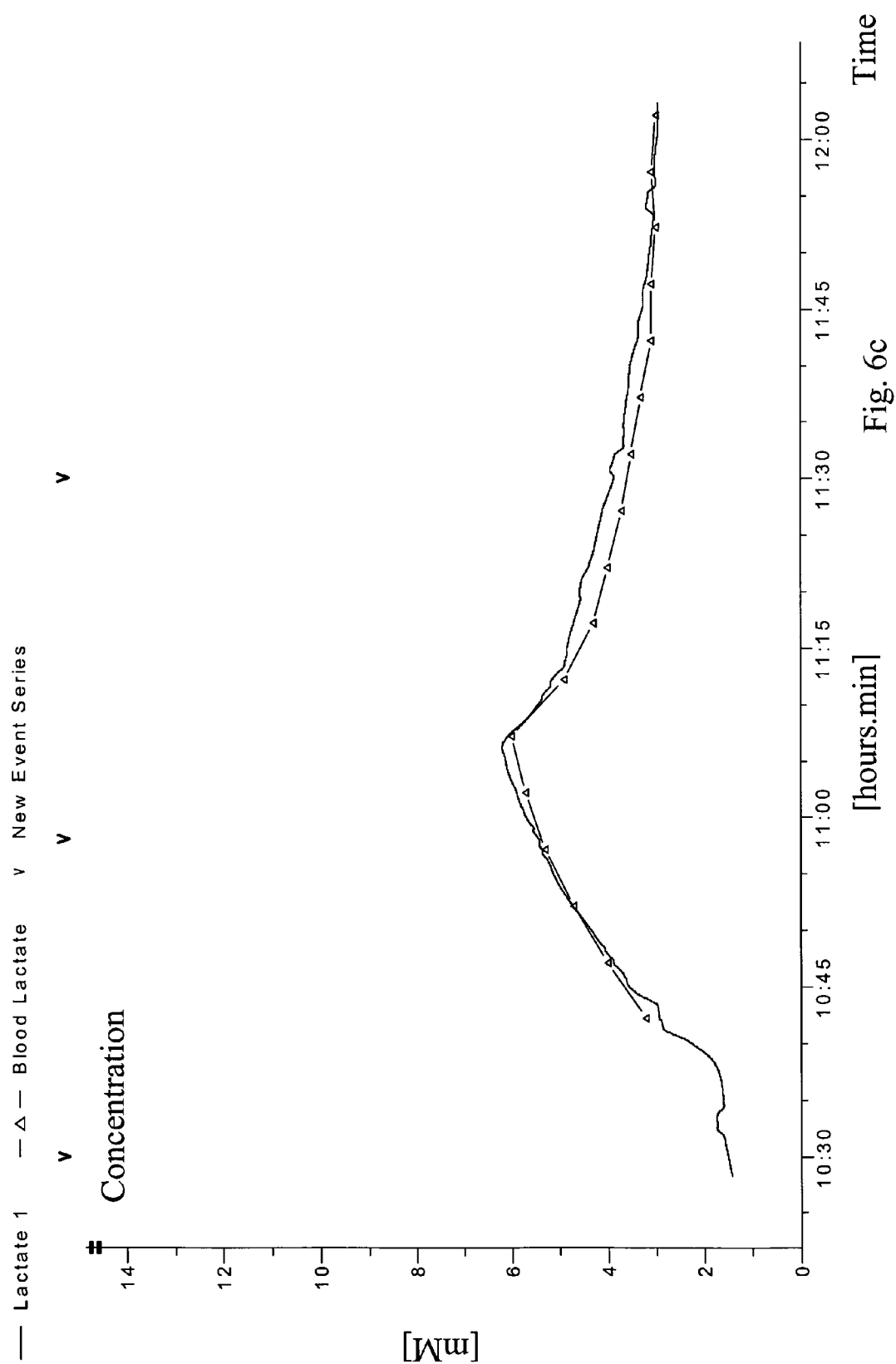
Figure 6D:
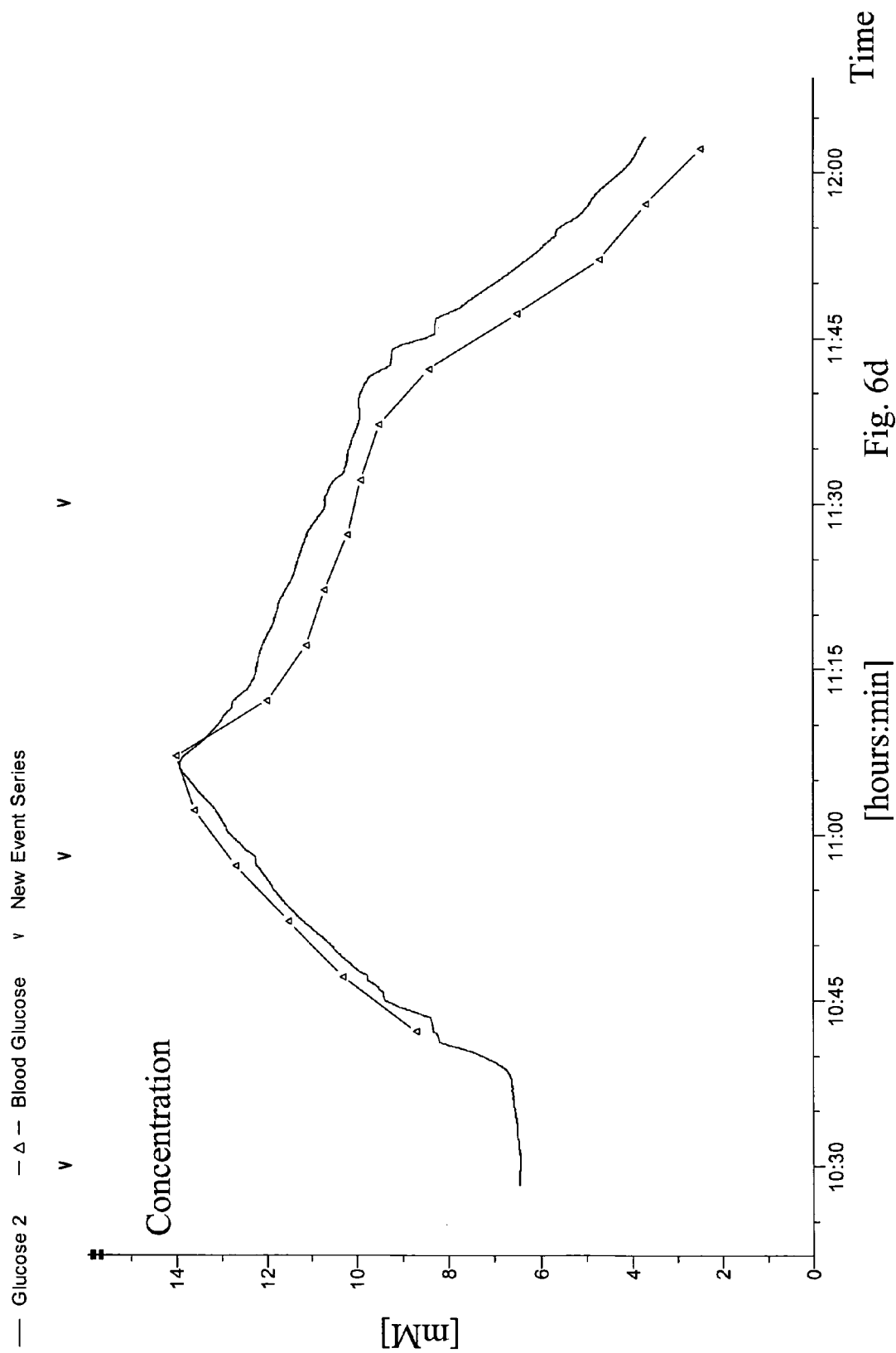
Figure 6E:
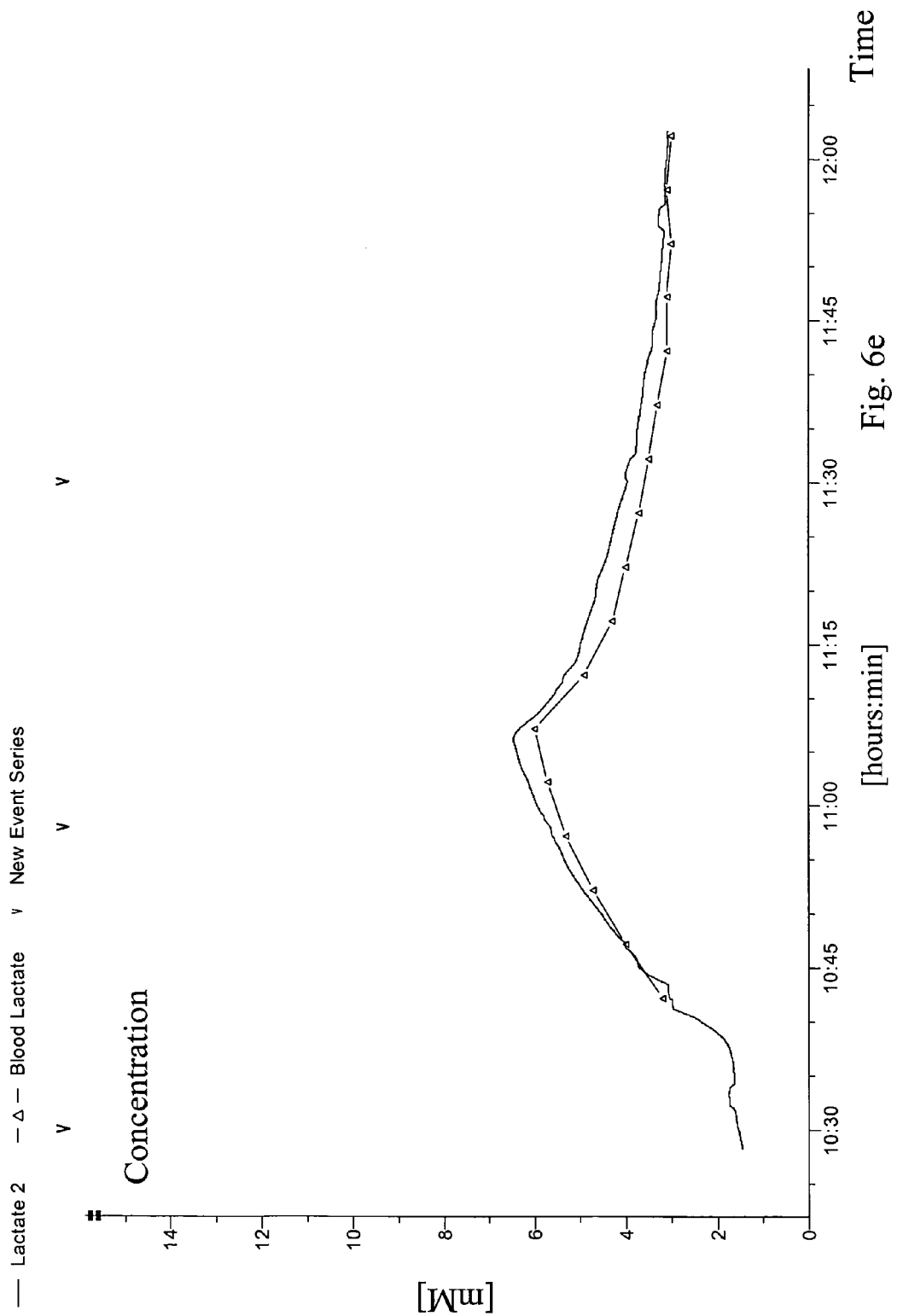
Figure 6F:
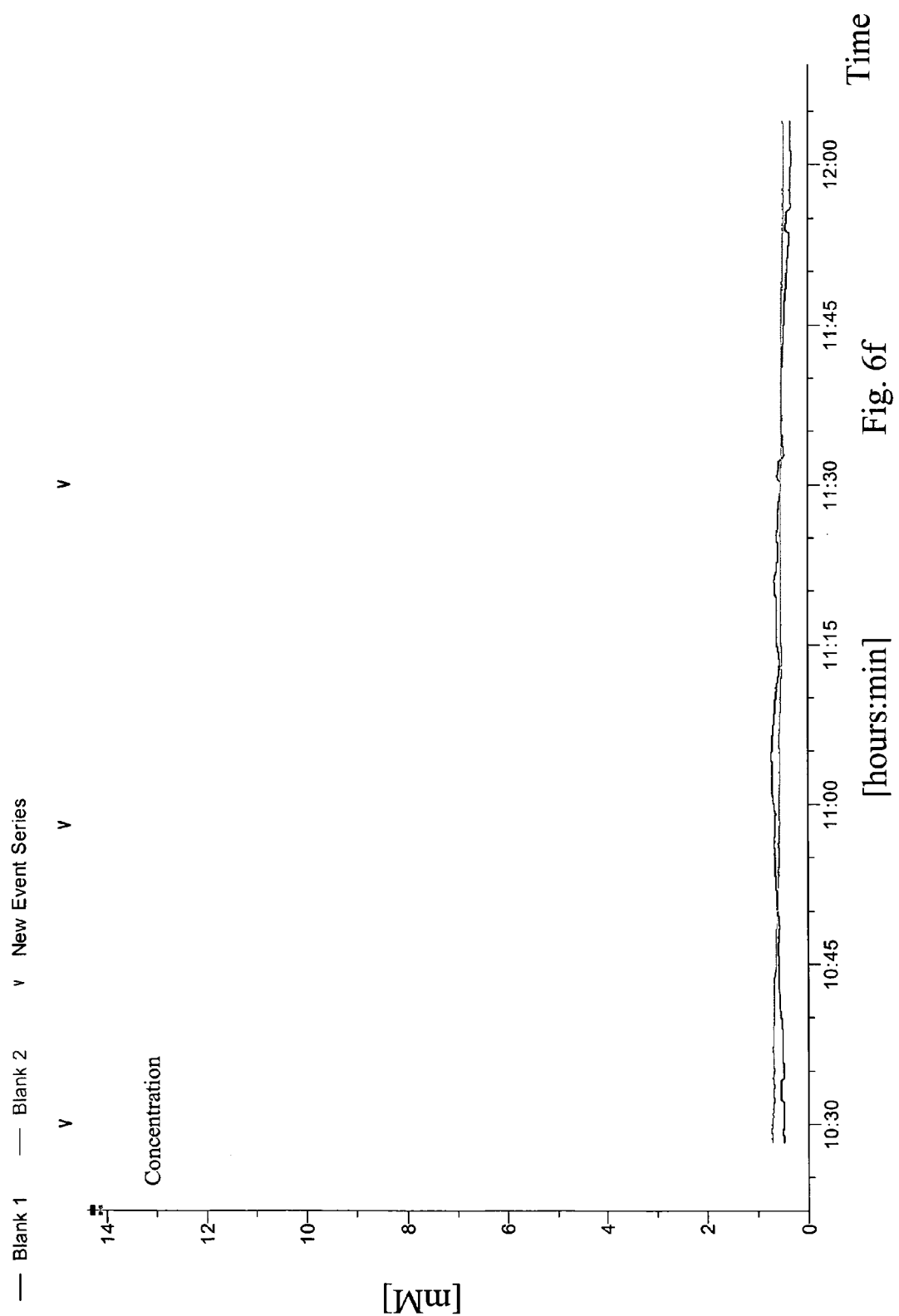

A system according to the present invention was tested in an animal, pig, model and the results are demonstrated in FIGS. 6a-6f. Time is shown on the X-axis and concentration in millimolar (mM) or millimol per liter is shown on the Y-axis. The test animal was infused with 50 ml of 20% lactate and 50 ml 30% glucose starting at 10:30. The infusion ended at 10:58. Injection of 30 Units of insulin was performed 11:30. Venous blood was sampled every 5 minutes during the infusion and assayed for glucose and lactate using a conventional blood gas analyzer. The blood gas data has been shifted about 12 minutes due to the delay, which was around 12 minutes, in the system/prototype. The results were obtained using a microdialysis probe inserted in a peripheral vein, the probe having a skin-out membrane with an active length of about 20 mm, an outer diameter (OD) of about 0.59 mm and a liquid permeability of about $2 \times 10^{-4}$ cm/bar×s at a perfusion flow of 0.5 microliters/minute. A flow through sensor with duplicate measuring electrodes, for glucose and lactate, and two blank electrodes was used with the following flow channel dimensions: height 75 micrometers and width 450 micrometers, and with each electrode having an area of 0.16 square millimeters, and was attached to the outlet of the microdialysis probe. The sensor followed the dimensions earlier given as preferred embodiments. The sensor signal was at about 1 Hz and the results presented are running average values based on 60 samples. The results of FIGS. 6a-6f demonstrates that the system has excellent accuracy, compared to blood gas data, and a delay time that is operable for using the system for monitoring in a critical care unit. It is also to be noticed that the measurement curves from the two glucose measuring electrodes respectively the two lactate measuring electrodes follow each other very closely. In FIG. 6a all measurement curves are displayed in the same diagram for ease of comparison and in FIGS. 6b-6f the measurement curves from the different measuring electrodes are shown separately for increased clarity.

Figure 7:
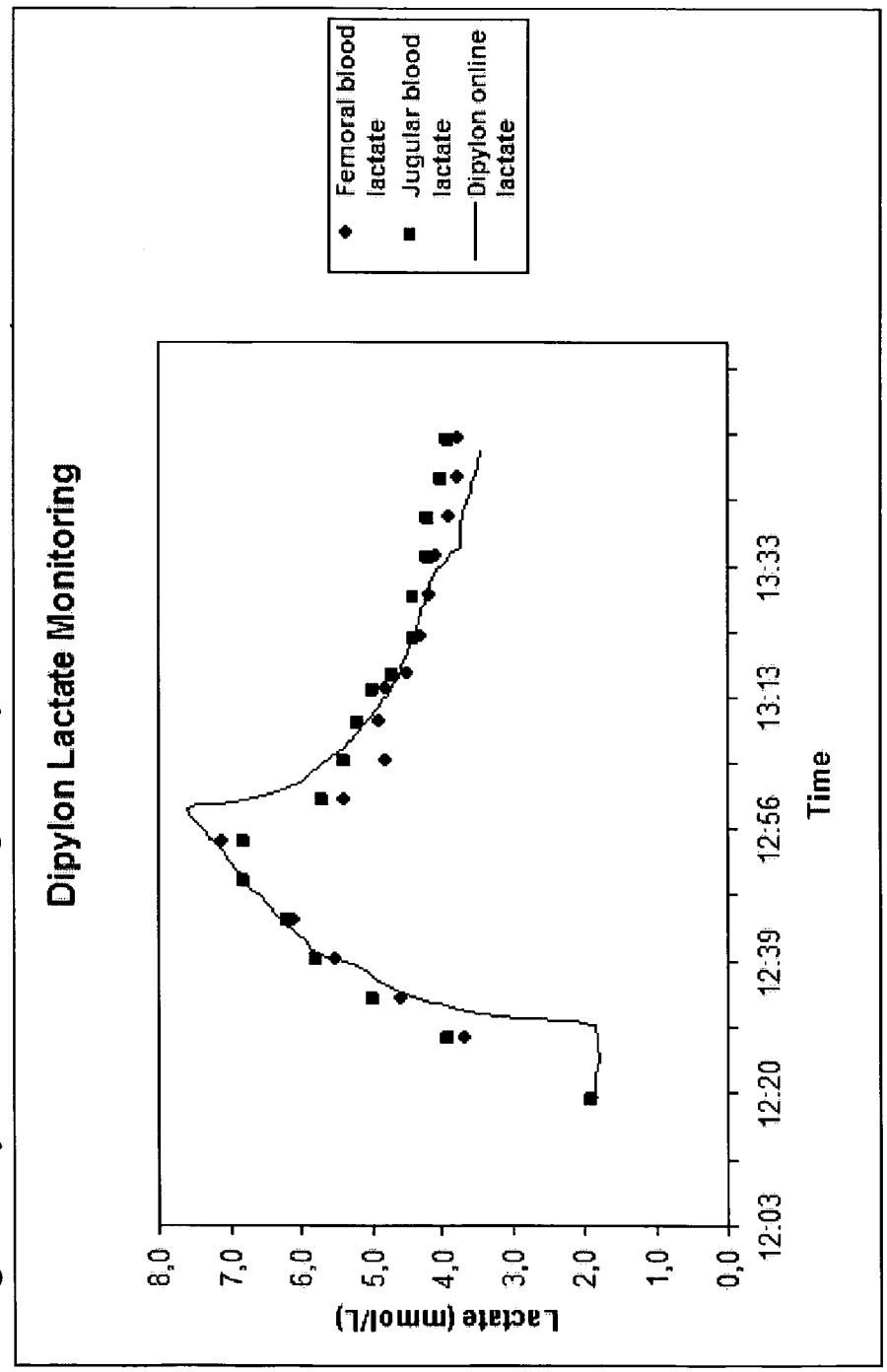
FIG. 7 demonstrates results with a system according to the invention from venous blood of a test animal.

A system according to the present invention was tested in an animal (pig) model and the results are demonstrated in FIG. 7, showing lactate data. Time is shown on the X-axis and concentration in millimol per liter (mmol/L) is shown on the Y-axis. The test animal was infused in the femoral vein with 50 ml of 20% lactate and 50 ml 30% glucose starting at 12:30. The infusion ended at 13:00. Venous blood was sampled every 5 minutes both from the femoral vein and the jugular vein and assayed for glucose and lactate using a conventional blood gas analyzer. The delay in the system was around 2 minutes. The results were obtained using a 67 cm long microdialysis probe inserted into the jugular vein and then guided to the vena cava superior, the probe having a skin-out membrane being around 40 mm long (active length) and around 1.55 mm in outer diameter (OD), with a liquid permeability of about $2 \times 10^{-4}$ cm/bar$^x$s (Lp=2) at a perfusion flow of about 10 microliters per minute. A flow through sensor with duplicate measuring electrodes (for glucose and lactate) and two blank electrodes was used with the following flow channel dimensions: height 75 micrometers and width 450 micrometers, and with each electrode having an area of 0.16 square millimeters, was attached to the outlet of the microdialysis probe. The sensor followed the dimensions earlier given as preferred embodiments. The sensor signal was at about 1 Hz and the results presented are running average values based on 60 samples. The results of FIG. 7, showing lactate data, demonstrate that the system has excellent accuracy (compared to blood gas data) and a delay time that is operable for using the system for monitoring a patient in a critical situation, e.g. during or after surgery or in an intensive care unit. It is also to be noticed that the measurement curve from the lactate measuring of the system follow the measurement values from the two blood gas measurements, which are used as references, very closely. Glucose values are not presented in FIG. 7, but showed the same excellent accuracy as for lactate.

Figure 8A:
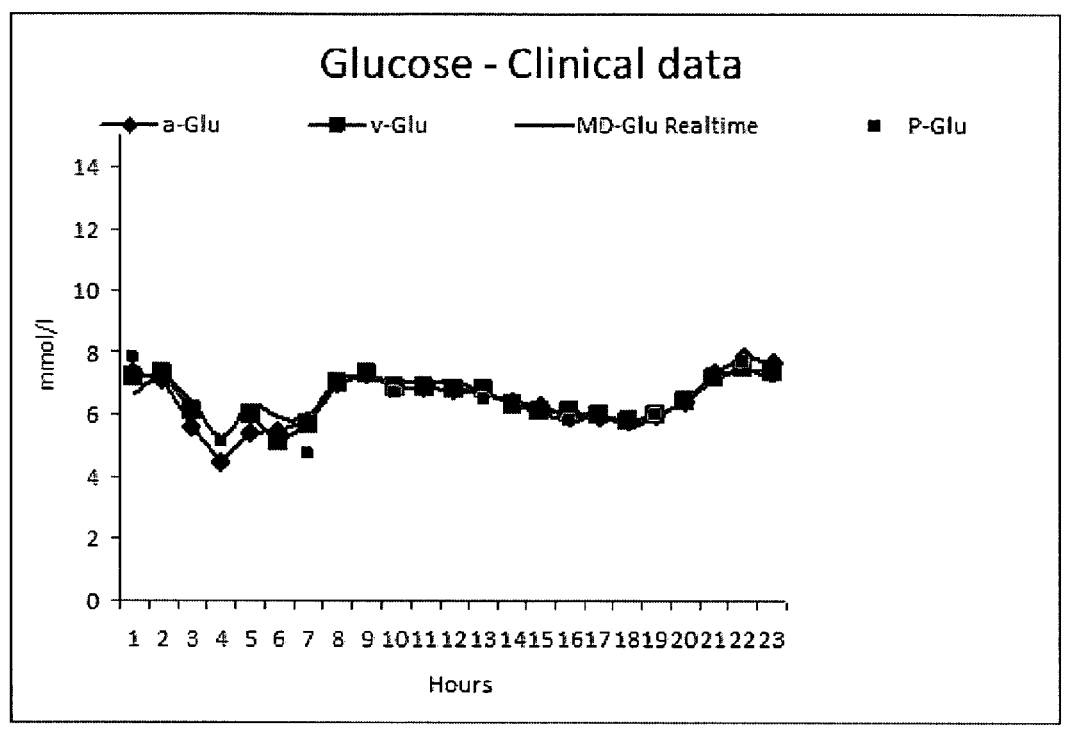
FIGS. 8a and 8b demonstrate results with the system in a clinical human setting.
Figure 8B:
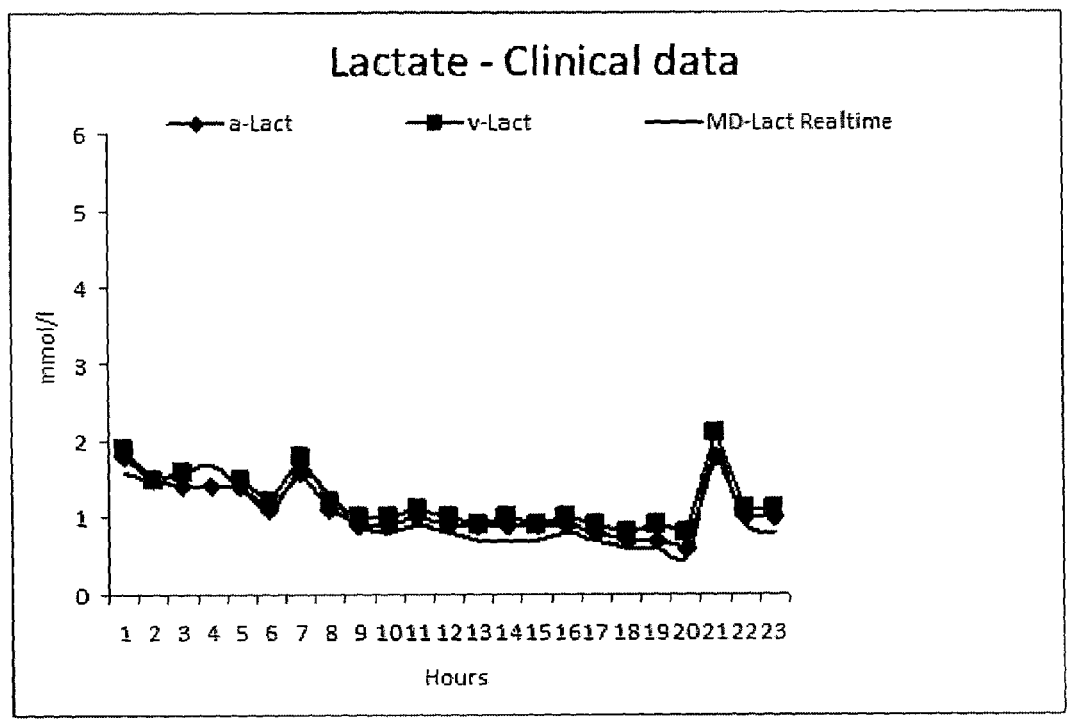

The system described above in the context of animal tests was used clinically with human patients. Results of glucose and lactate values are presented in FIGS. 8a 8b, respectively. The flow rate was 6.7 microliters per minute. Arterial and venous glucose and lactate were sampled each hour, while also plasma glucose was sample each third hour. FIGS. 8a and 8b comparatively shows glucose and lactate values in real-time from the system according to the present invention. The results demonstrate that the inventive system has excellent accuracy and provides physicians continuously with valuable patient information without cumbersome and delaying sampling and analyzing in a blood gas measuring equipment. Accordingly, the inventive system admits that critical care patients can be treated more proactively which potentially can reduce treatment times and may have lifesaving consequences.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

The invention claimed is:

1. A measuring system for measuring the concentration of substances or analytes in a body fluid or in a body tissue, comprising:
    a microdialysis probe comprising a multilumen tube and a microdialysis membrane, said tube having at least two longitudinally arranged inner bores, said bores extending from a proximal end of the tube to a distal end of the tube, at least two channels, one from each of said at least two bores to the outside of said tube, wherein said bores are blocked for passage of liquid distally of the respective channels, and a tubular membrane arranged circumferentially around the tube such as to cover the at least two channels, wherein said membrane is sealingly fastened to the tube thereby forming a space between the tube and the membrane, and wherein the probe is beth adapted to be placed in blood or in tissue,
    a flow through sensor for analysing a fluid having passed said microdialysis probe,
    a pump for pumping said fluid to and through said microdialysis probe and further to and through said sensor, and
    tubing connecting said pump to said microdialysis probe and said microdialysis probe to said sensor,
    said pump effecting a flow rate in said system in the interval 0.2-15 microliters per minute, wherein the sensor comprises a flow channel having a flow resistance or pressure drop adapted to the characteristics of the microdialysis membrane so as to eliminate, or at least substantially reduce, ultra filtering in the microdialysis membrane.

2. A measuring system according claim 1, wherein the cross-sectional area of the flow channel is adapted to one or more characteristics of the microdialysis membrane, said characteristics comprising at least one of the microdialysis membrane area and the liquid permeability of the microdialysis membrane.

3. A measuring system according to claim 2, wherein the microdialysis membrane area is between 20 to 200 mm$^2$.

4. A measuring system according to claim 2, wherein the liquid permeability of the microdialysis membrane is between 1 to $3\times10^{-4}$ cm/bar×s.

5. A measuring system according to claim 1, wherein said the flow channel has a flow resistance or pressure drop less than about 100 Pa at a flow rate of about 0.5 microliters per minute.

6. A measuring system according to claim 5 that is essentially free from ultrafiltration when operated with a flow rate of about 0.5 microliters/minute when continuously measuring and monitoring physiologically and clinically relevant levels of glucose and/or lactate with a sensor having a sensor flow resistance or pressure drop of less than about 100 Pa, wherein the microdialysis membrane has an extension of about 30 mm active length and a liquid (hydraulic) permeability of about $2\times10^{-4}$ cm/bar×s; and the sensor flow channel has a flow channel with width of about 550 micrometer.

7. A measuring system according to claim 6, wherein the flow channel length is about 7.5 mm.

8. A measuring system according to claim 1, wherein the flow channel has a flow resistance or pressure drop less than about 1.6 kPa at a flow rate of about 10 microliters per minute.

9. A measuring system according to claim 8 that is essentially free from ultrafiltration when operated with a flow rate of about 10 microliters/minute when continuously measuring and monitoring physiologically and clinically relevant levels of glucose and/or lactate with a sensor having a sensor flow resistance or pressure drop of less than about 1.6 kPa, wherein the microdialysis membrane has an extension of about 40 mm active length and a liquid (hydraulic) permeability of about $2\times10^{-4}$ cm/bar×s; and the sensor flow channel has a flow channel with width of about 550 micrometer.

10. A measuring system according to claim 9, wherein the flow channel length is about 7.5 mm.

11. A measuring system according to claim 1, wherein said flow channel has a flow channel width in the interval of 250-1000 micrometer and a flow channel height in the interval of 10 micrometer to 1 millimeter.

12. A measuring system according to claim 11, wherein the flow channel height is 25-100 micrometer.

13. A measuring system according to claim 11, wherein the flow channel width is about 550 micrometer and the flow channel height is about 75 micrometer.

14. A measuring system according to claim 1, wherein said sensor includes at least one measuring electrode with multiple membrane layers, wherein said layers comprise:
    an oxidase membrane layer comprising immobilized oxidase enzyme capable of reacting the analyte with oxygen in a hydrogen peroxide generating reaction; and
    a diffusion limiting membrane adapted to provide a higher diffusion resistance for the analyte than for oxygen and to provide lower flow of analyte to the oxidase membrane layer than the conversion rate of the oxidase enzyme.

15. A measuring system according to claim 14, wherein the diffusion limiting membrane has a thickness of about 10 micrometer.

16. A measuring system according to claim 14, wherein the diffusion limiting membrane is made from a hydrogel.

17. A measuring system according to claim 16, wherein the hydrogel is poly-HEMA.

18. A measuring system according to claim 14, wherein the oxidase membrane layer has an area adapted so that the output signal of said measuring electrode is sufficiently high relative to a potential noise level or noise signal for the lowest analyte concentration in the linear measurement range of the measuring electrode.

19. A measuring system according to claim 14, wherein said oxidase membrane layer has an essentially circular area with a diameter from about 250 to about 1000 micrometer.

20. A measuring system according to claim 19, wherein said oxidase membrane layer has an essentially circular area with a diameter of about 450 micrometer.

21. A measuring system according to claim 14, wherein the oxidase is glucose oxidase and/or lactate oxidase.

22. A measuring system according to claim 1, wherein said sensor further comprises a catalase membrane with a sufficient extension and catalase activity to substantially decompose all the hydrogen peroxide reaching the membrane.

23. A measuring system according to claim 22, wherein said catalase membrane has a thickness in the interval of 5 to 10 micrometer.

24. A measuring system according to claim 1, comprising several consecutively arranged measuring electrodes, wherein each measuring electrode comprises multiple membrane layers, wherein said layers comprise:
   an oxidase membrane layer comprising immobilized oxidase enzyme capable of reacting the analyte with oxygen in a hydrogen peroxide generating reaction; and
   a diffusion limiting membrane adapted to provide a higher diffusion resistance for the analyte than for oxygen and to provide lower flow of analyte to the oxidase membrane layer than the conversion rate of the oxidase enzyme.

25. A measuring system according to claim 1, wherein the microdialysis membrane has a size selective layer located on its outside and facing body fluid when the probe is place in blood or tissue.

26. A measuring system according to claim 1, wherein a waste container is connected to an outflow end of said flow channel for collecting fluid flowing out from said flow channel, said waste container comprising an absorbent.

27. A measuring system according to claim 26, wherein said waste container comprises means adapted for connection to a receptacle for collecting fluid in said receptacle for further analysis of said fluid.

28. A measuring system according to claim 26, wherein the absorbent is anti-bacterial.

29. A measuring system for measuring the concentration of substances or analytes in a body fluid or in a body tissue, comprising:
   a microdialysis probe comprising a microdialysis membrane, wherein the probe is adapted to be placed in blood or in tissue,
   a flow through sensor for analysing a fluid having passed said microdialysis probe,
   a pump for pumping said fluid to and through said microdialysis probe and further to and through said sensor,
   tubing connecting said pump to said microdialysis probe and said microdialysis probe to said sensor, and
   a waste container connected to an outflow end of said flow channel for collecting fluid flowing out from said flow channel, said waste container comprising an absorbent and a pressure relief valve
   said pump effecting a flow rate in said system in the interval 0.2-15 microliters per minute,
wherein the sensor comprises a flow channel having a flow resistance or pressure drop adapted to the characteristics of the microdialysis membrane so as to eliminate, or at least substantially reduce, ultra filtering in the microdialysis membrane.

30. A measuring system according to claim 29, wherein said pressure relief valve is impermeable to bacteria.

31. A measuring system according claim 29, wherein the cross-sectional area of the flow channel is adapted to one or more characteristics of the microdialysis membrane, said characteristics comprising at least one of the microdialysis membrane area and the liquid permeability of the microdialysis membrane.

32. A measuring system according to claim 31, wherein the microdialysis membrane area is between 20 to 200 mm$^2$.

33. A measuring system according to claim 31, wherein the liquid permeability of the microdialysis membrane is between 1 to $3 \times 10^{-4}$ cm/bar×s.

34. A measuring system according to claim 29, wherein said the flow channel has a flow resistance or pressure drop less than about 100 Pa at a flow rate of about 0.5 microliters per minute.

35. A measuring system according to claim 34 that is essentially free from ultrafiltration when operated with a flow rate of about 0.5 microliters/minute when continuously measuring and monitoring physiologically and clinically relevant levels of glucose and/or lactate with a sensor having a sensor flow resistance or pressure drop of less than about 100 Pa, wherein the microdialysis membrane has an extension of about 30 mm active length and a liquid (hydraulic) permeability of about $2 \times 10^{-4}$ cm/bar×s; and the sensor flow channel has a flow channel with width of about 550 micrometer.

36. A measuring system according to claim 35, wherein the flow channel length is about 7.5 mm.

37. A measuring system according to claim 29, wherein the flow channel has a flow resistance or pressure drop less than about 1.6 kPa at a flow rate of about 10 microliters per minute.

38. A measuring system according to claim 37 that is essentially free from ultrafiltration when operated with a flow rate of about 10 microliters/minute when continuously measuring and monitoring physiologically and clinically relevant levels of glucose and/or lactate with a sensor having a sensor flow resistance or pressure drop of less than about 1.6 kPa, wherein the microdialysis membrane has an extension of about 40 mm active length and a liquid (hydraulic) permeability of about $2 \times 10^{-4}$ cm/bar×s; and the sensor flow channel has a flow channel with width of about 550 micrometer.

39. A measuring system according to claim 38, wherein the flow channel length is about 7.5 mm.

40. A measuring system according to claim 29, wherein said flow channel has a flow channel width in the interval of 250-1000 micrometer and a flow channel height in the interval of 10 micrometer to 1 millimeter.

41. A measuring system according to claim 40, wherein the flow channel height is 25-100 micrometer.

42. A measuring system according to claim 40, wherein the flow channel width is about 550 micrometer and the flow channel height is about 75 micrometer.

43. A measuring system according to claim 29, wherein said sensor includes at least one measuring electrode with multiple membrane layers, wherein said layers comprise:
   an oxidase membrane layer comprising immobilized oxidase enzyme capable of reacting the analyte with oxygen in a hydrogen peroxide generating reaction; and
   a diffusion limiting membrane adapted to provide a higher diffusion resistance for the analyte than for oxygen and to provide lower flow of analyte to the oxidase membrane layer than the conversion rate of the oxidase enzyme.

44. A measuring system according to claim 43, wherein the diffusion limiting membrane has a thickness of about 10 micrometer.

45. A measuring system according to claim 43, wherein the diffusion limiting membrane is made from a hydrogel.

46. A measuring system according to claim 45, wherein the hydrogel is poly-HEMA.

47. A measuring system according to claim 43, wherein the oxidase membrane layer has an area adapted so that the output signal of said measuring electrode is sufficiently high relative to a potential noise level or noise signal for the lowest analyte concentration in the linear measurement range of the measuring electrode.

48. A measuring system according to claim 43, wherein said oxidase membrane layer has an essentially circular area with a diameter from about 250 to about 1000 micrometer.

49. A measuring system according to claim 48, wherein said oxidase membrane layer has an essentially circular area with a diameter of about 450 micrometer.

50. A measuring system according to claim 43, wherein the oxidase is glucose oxidase and/or lactate oxidase.

51. A measuring system according to claim 29, wherein said sensor further comprises a catalase membrane with a sufficient extension and catalase activity to substantially decompose all the hydrogen peroxide reaching the membrane.

52. A measuring system according to claim 51, wherein said catalase membrane has a thickness in the interval of 5 to 10 micrometer.

53. A measuring system according to claim 29, comprising several consecutively arranged measuring electrodes, wherein each measuring electrode comprises multiple membrane layers, wherein said layers comprise:

an oxidase membrane layer comprising immobilized oxidase enzyme capable of reacting the analyte with oxygen in a hydrogen peroxide generating reaction; and a diffusion limiting membrane adapted to provide a higher diffusion resistance for the analyte than for oxygen and to provide lower flow of analyte to the oxidase membrane layer than the conversion rate of the oxidase enzyme.

54. A measuring system according to claim 29, wherein the microdialysis membrane has a size selective layer located on its outside and facing body fluid when the probe is place in blood or tissue.

55. A measuring system according to claim 29, wherein said waste container comprises means adapted for connection to a receptacle for collecting fluid in said receptacle for further analysis of said fluid.

56. A measuring system according to claim 29, wherein the absorbent is anti-bacterial.

57. A measuring system according to claim according to claim 29, wherein the microdialysis probe comprises a multilumen tube and a microdialysis membrane, said tube having at least two longitudinally arranged inner bores, said bores extending from a proximal end of the tube to a distal end of the tube, at least two channels, one from each of said at least two bores to the outside of said tube, wherein said bores are blocked for passage of liquid distally of the respective channels, and a tubular membrane arranged circumferentially around the tube such as to cover the at least two channels, wherein said membrane is sealingly fastened to the tube thereby forming a space between the tube and the membrane.

* * * * *

UNITED STATES PATENT AND TRADEMARK OFFICE
CERTIFICATE OF CORRECTION

PATENT NO. : 9,101,304 B2  
APPLICATION NO. : 13/000708  
DATED : August 11, 2015  
INVENTOR(S) : Stefan Lindgren et al.

It is certified that error appears in the above-identified patent and that said Letters Patent is hereby corrected as shown below:

In the Claims

Claim 1, Column 19, Line 51, delete "beth".

Claim 33, Column 22, Line 16, change "cm/bar×s" to --cm/bar × s--.

Claim 35, Column 22, Line 29, change "cm/bar×s" to --cm/bar × s--.

Signed and Sealed this  
Twenty-eighth Day of June, 2016

Michelle K. Lee  
*Director of the United States Patent and Trademark Office*